United States Patent
Eng et al.

(10) Patent No.: US 10,589,057 B2
(45) Date of Patent: Mar. 17, 2020

(54) ENHANCING USER SLEEP CYCLE

(71) Applicant: Comcast Cable Communications, LLC, Philadelphia, PA (US)

(72) Inventors: Adam Eng, Golden, CO (US); Glenn Barnett, Aurora, CO (US)

(73) Assignee: Comcast Cable Communications, LLC, Philadelphia, PA (US)

( * ) Notice: Subject to any disclaimer, the term of this patent is extended or adjusted under 35 U.S.C. 154(b) by 0 days.

(21) Appl. No.: 15/624,806

(22) Filed: Jun. 16, 2017

(65) Prior Publication Data
US 2018/0361109 A1   Dec. 20, 2018

(51) Int. Cl.
*A61M 21/02* (2006.01)
*G09G 5/02* (2006.01)
*G09G 5/10* (2006.01)
*G06F 3/147* (2006.01)
*A61M 21/00* (2006.01)

(52) U.S. Cl.
CPC ............. *A61M 21/02* (2013.01); *G06F 3/147* (2013.01); *G09G 5/02* (2013.01); *G09G 5/10* (2013.01); *A61M 2021/005* (2013.01); *A61M 2021/0027* (2013.01); *A61M 2205/3553* (2013.01); *A61M 2205/3584* (2013.01); *G09G 2320/0626* (2013.01); *G09G 2380/08* (2013.01)

(58) Field of Classification Search
None
See application file for complete search history.

(56) References Cited

U.S. PATENT DOCUMENTS

| 2006/0152525 | A1* | 7/2006 | Woog | G09G 5/003 345/589 |
| 2015/0070337 | A1* | 3/2015 | Bell | G09G 3/2003 345/207 |
| 2015/0342511 | A1* | 12/2015 | Goldberg | G06Q 50/22 434/236 |
| 2017/0318345 | A1* | 11/2017 | Branton-Housley | H04N 21/478 |

OTHER PUBLICATIONS f.lux software to make your life better, 2 pages, <www.justgetflux.com>, As retrieved on Aug. 28, 2017.
f.lux: sleep research, 4 pages, <https://justgetflux.com/research.html>, As retrieved on Aug. 28, 2017.

* cited by examiner

*Primary Examiner* — YuJang Tswei
(74) *Attorney, Agent, or Firm* — Banner & Witcoff, Ltd.

(57) ABSTRACT

Methods are disclosed for receiving and processing video content to aid in a user's rest cycles, such as sleep and wake cycles. Video content may be received and processed to determine information related to a plurality of pixels to be displayed on a screen. Each of the plurality of pixels may have a corresponding color value. A time of day when the video content is to be displayed is determined, and compared to a current time of day. Based on the comparison or other data, a color value of one or more of the pixels can be adjusted or changed.

20 Claims, 21 Drawing Sheets

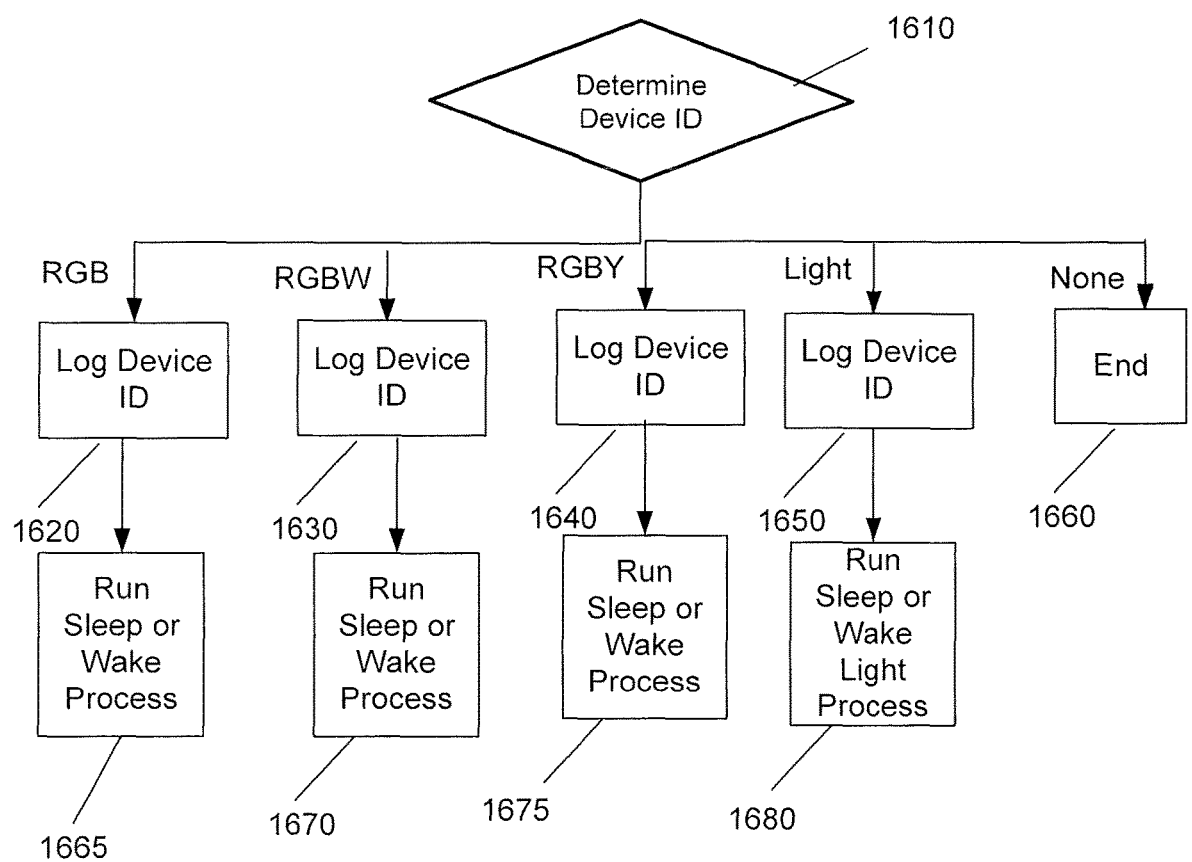

FIG. 17

| R (Initial) | P (R) | R (Final) | G (Initial) | P (G) | G (Final) | B (Initial) | P (B) | B (Final) | HEX | Color |
|---|---|---|---|---|---|---|---|---|---|---|
| 102 | 0 | 102 | 102 | 0 | 102 | 204 | 0 | 204 | 6666CC | Purple-Blue |
| 102 | 5 | 105 | 102 | 5 | 105 | 204 | 5 | 200 | 6969C8 | Purple-Blue |
| 102 | 10 | 108 | 102 | 10 | 108 | 204 | 10 | 196 | 6C6CC4 | Purple-Blue |
| 102 | 15 | 111 | 102 | 15 | 111 | 204 | 15 | 192 | 6F6FC0 | Purple-Blue |
| 102 | 20 | 114 | 102 | 20 | 114 | 204 | 20 | 188 | 7272BC | Lavender |
| 102 | 25 | 117 | 102 | 25 | 117 | 204 | 25 | 184 | 7575B8 | Lavender |
| 102 | 30 | 120 | 102 | 30 | 120 | 204 | 30 | 180 | 7878B4 | Lavender |
| 102 | 35 | 123 | 102 | 35 | 123 | 204 | 35 | 176 | 7B7BB0 | Lavender |
| 102 | 40 | 126 | 102 | 40 | 126 | 204 | 40 | 172 | 7E7EAC | Gray |
| 102 | 45 | 129 | 102 | 45 | 129 | 204 | 45 | 168 | 8181A8 | Gray |
| 102 | 50 | 132 | 102 | 50 | 132 | 204 | 50 | 164 | 8484A4 | Gray |
| 102 | 55 | 135 | 102 | 55 | 135 | 204 | 55 | 160 | 8787A0 | Gray |
| 102 | 60 | 138 | 102 | 60 | 138 | 204 | 60 | 156 | 8A8A9C | Gray |
| 102 | 65 | 141 | 102 | 65 | 141 | 204 | 65 | 152 | 8D8D98 | Gray |
| 102 | 70 | 144 | 102 | 70 | 144 | 204 | 70 | 148 | 909094 | Gray |
| 102 | 75 | 147 | 102 | 75 | 72 | 204 | 75 | 144 | 934890 | Light Red |
| 102 | 80 | 150 | 102 | 80 | 70 | 204 | 80 | 140 | 96468C | Light Red |
| 102 | 85 | 153 | 102 | 85 | 68 | 204 | 85 | 136 | 994488 | Light Red |
| 102 | 90 | 156 | 102 | 90 | 66 | 204 | 90 | 132 | 9C4284 | Light Red |
| 102 | 95 | 159 | 102 | 95 | 64 | 204 | 95 | 128 | 9F4080 | Light Red |
| 102 | 100 | 162 | 102 | 100 | 62 | 204 | 100 | 124 | A23E7C | Light Red |
| 102 | 105 | 165 | 102 | 105 | 60 | 204 | 105 | 120 | A53C78 | Light Red |
| 102 | 110 | 168 | 102 | 110 | 58 | 204 | 110 | 116 | A83A74 | Light Red |
| 102 | 115 | 171 | 102 | 115 | 56 | 204 | 115 | 112 | AB3870 | Red |
| 102 | 120 | 174 | 102 | 120 | 54 | 204 | 120 | 108 | AE366C | Red |
| 102 | 125 | 177 | 102 | 125 | 52 | 204 | 125 | 104 | B13468 | Red |
| 102 | 130 | 180 | 102 | 130 | 50 | 204 | 130 | 100 | B43264 | Red |
| 102 | 135 | 183 | 102 | 135 | 48 | 204 | 135 | 96 | B73060 | Red |
| 102 | 140 | 186 | 102 | 140 | 46 | 204 | 140 | 92 | BA2E5C | Red |
| 102 | 145 | 189 | 102 | 145 | 44 | 204 | 145 | 88 | BD2C58 | Red |
| 102 | 150 | 192 | 102 | 150 | 42 | 204 | 150 | 84 | C02A54 | Red |
| 102 | 155 | 195 | 102 | 155 | 40 | 204 | 155 | 80 | C32850 | Red |
| 102 | 160 | 198 | 102 | 160 | 38 | 204 | 160 | 76 | C6264C | Red |
| 102 | 165 | 201 | 102 | 165 | 36 | 204 | 165 | 72 | C92448 | Red |
| 102 | 170 | 204 | 102 | 170 | 34 | 204 | 170 | 68 | CC2244 | Red |
| 102 | 175 | 207 | 102 | 175 | 32 | 204 | 175 | 64 | CF2040 | Red |
| 102 | 180 | 210 | 102 | 180 | 30 | 204 | 180 | 60 | D21E3C | Red |
| 102 | 185 | 213 | 102 | 185 | 28 | 204 | 185 | 56 | D51C38 | Red |
| 102 | 190 | 216 | 102 | 190 | 26 | 204 | 190 | 52 | D81A34 | Red |
| 102 | 195 | 219 | 102 | 195 | 24 | 204 | 195 | 48 | DB1830 | Red |
| 102 | 200 | 222 | 102 | 200 | 22 | 204 | 200 | 44 | DE162C | Deep Red |
| 102 | 205 | 225 | 102 | 205 | 20 | 204 | 205 | 40 | E11428 | Deep Red |
| 102 | 210 | 228 | 102 | 210 | 18 | 204 | 210 | 36 | E41224 | Deep Red |
| 102 | 215 | 231 | 102 | 215 | 16 | 204 | 215 | 32 | E71020 | Deep Red |
| 102 | 220 | 234 | 102 | 220 | 14 | 204 | 220 | 28 | EA0E1C | Deep Red |
| 102 | 225 | 237 | 102 | 225 | 12 | 204 | 225 | 24 | ED0C18 | Deep Red |
| 102 | 230 | 240 | 102 | 230 | 10 | 204 | 230 | 20 | F00A14 | Deep Red |
| 102 | 235 | 243 | 102 | 235 | 8 | 204 | 235 | 16 | F30810 | Deep Red |
| 102 | 240 | 246 | 102 | 240 | 6 | 204 | 240 | 12 | F6060C | Deep Red |
| 102 | 245 | 249 | 102 | 245 | 4 | 204 | 245 | 8 | F90408 | Deep Red |
| 102 | 250 | 252 | 102 | 250 | 2 | 204 | 250 | 4 | FC0204 | Deep Red |
| 102 | 255 | 255 | 102 | 255 | 0 | 204 | 255 | 0 | FF0000 | Deep Red |

FIG. 19

| R (Initial) | P (R) | R (Final) | G (Initial) | P (G) | G (Final) | B (Initial) | P (B) | B (Final) | HEX | Color |
|---|---|---|---|---|---|---|---|---|---|---|
| 50 | 0 | 50 | 100 | 0 | 100 | 150 | 0 | 150 | 326496 | Blue |
| 50 | 5 | 54 | 100 | 5 | 103 | 150 | 5 | 147 | 366793 | Blue |
| 50 | 10 | 58 | 100 | 10 | 106 | 150 | 10 | 144 | 3A6A90 | Blue |
| 50 | 15 | 62 | 100 | 15 | 109 | 150 | 15 | 141 | 3E6D8D | Blue |
| 50 | 20 | 66 | 100 | 20 | 112 | 150 | 20 | 138 | 42708A | Blue-Green |
| 50 | 25 | 70 | 100 | 25 | 115 | 150 | 25 | 135 | 467387 | Blue-Green |
| 50 | 30 | 74 | 100 | 30 | 118 | 150 | 30 | 132 | 4A7684 | Blue-Green |
| 50 | 35 | 78 | 100 | 35 | 121 | 150 | 35 | 129 | 4E7981 | Blue-Green |
| 50 | 40 | 82 | 100 | 40 | 124 | 150 | 40 | 126 | 527C7E | Blue-Green |
| 50 | 45 | 86 | 100 | 45 | 127 | 150 | 45 | 123 | 567F7B | Green |
| 50 | 50 | 90 | 100 | 50 | 130 | 150 | 50 | 120 | 5A8278 | Green |
| 50 | 55 | 94 | 100 | 55 | 133 | 150 | 55 | 117 | 5E8575 | Green |
| 50 | 60 | 98 | 100 | 60 | 136 | 150 | 60 | 114 | 628872 | Green |
| 50 | 65 | 102 | 100 | 65 | 139 | 150 | 65 | 111 | 6688 6F | Light Green |
| 50 | 70 | 106 | 100 | 70 | 143 | 150 | 70 | 109 | 6A8F6D | Light Green |
| 50 | 75 | 110 | 100 | 75 | 71 | 150 | 75 | 106 | 6E476A | Light Red |
| 50 | 80 | 114 | 100 | 80 | 69 | 150 | 80 | 103 | 724567 | Light Red |
| 50 | 85 | 118 | 100 | 85 | 67 | 150 | 85 | 100 | 764364 | Light Red |
| 50 | 90 | 122 | 100 | 90 | 65 | 150 | 90 | 97 | 7A4161 | Light Red |
| 50 | 95 | 126 | 100 | 95 | 63 | 150 | 95 | 94 | 7E3F5E | Light Red |
| 50 | 100 | 130 | 100 | 100 | 61 | 150 | 100 | 91 | 82305B | Light Red |
| 50 | 105 | 134 | 100 | 105 | 59 | 150 | 105 | 88 | 863B58 | Light Red |
| 50 | 110 | 138 | 100 | 110 | 57 | 150 | 110 | 85 | 8A3955 | Red |
| 50 | 115 | 142 | 100 | 115 | 55 | 150 | 115 | 82 | 8E3752 | Red |
| 50 | 120 | 146 | 100 | 120 | 53 | 150 | 120 | 79 | 92354F | Red |
| 50 | 125 | 150 | 100 | 125 | 51 | 150 | 125 | 76 | 96334C | Red |
| 50 | 130 | 155 | 100 | 130 | 49 | 150 | 130 | 74 | 9B314A | Red |
| 50 | 135 | 159 | 100 | 135 | 47 | 150 | 135 | 71 | 9F2F47 | Red |
| 50 | 140 | 163 | 100 | 140 | 45 | 150 | 140 | 68 | A32D44 | Red |
| 50 | 145 | 167 | 100 | 145 | 43 | 150 | 145 | 65 | A72B41 | Red |
| 50 | 150 | 171 | 100 | 150 | 41 | 150 | 150 | 62 | AB293E | Deep Red |
| 50 | 155 | 175 | 100 | 155 | 39 | 150 | 155 | 59 | AF273B | Deep Red |
| 50 | 160 | 179 | 100 | 160 | 37 | 150 | 160 | 56 | B32538 | Deep Red |
| 50 | 165 | 183 | 100 | 165 | 35 | 150 | 165 | 53 | B72335 | Deep Red |

FIG. 21

| Time of Day | | | | Inensity Time Factor | Notes | Mode |
|---|---|---|---|---|---|---|
| Hours | Minutes | Seconds | Clock | | | |
| 0.5 | 30 | 1800 | 12:30 AM | 1.113636364 | (Spill over Calculation) | Sleep |
| 1 | 60 | 3600 | 1:00 AM | 1.136363636 | Extra Ramp down time (Max) | Sleep |
| 1.5 | 90 | 5400 | 1:30 AM | 0 | | |
| 2 | 120 | 7200 | 2:00 AM | 0 | | |
| 2.5 | 150 | 9000 | 2:30 AM | 0 | | |
| 3 | 180 | 10800 | 3:00 AM | 0 | | |
| 3.5 | 210 | 12600 | 3:30 AM | 0 | | |
| 4 | 240 | 14400 | 4:00 AM | 0 | | |
| 4.5 | 270 | 16200 | 4:30 AM | 0 | | |
| 5 | 300 | 18000 | 5:00 AM | 1.4 | Turn on TV 2 hours early, so extra intensity shift (Max) | Wake |
| 5.5 | 330 | 19800 | 5:30 AM | 1.272727273 | | Wake |
| 6 | 360 | 21600 | 6:00 AM | 1.166666667 | | Wake |
| 6.5 | 390 | 23400 | 6:30 AM | 1.076923077 | | Wake |
| 7 | 420 | 25200 | 7:00 AM | 1 | Normal Screen on time | Wake |
| 7.5 | 450 | 27000 | 7:30 AM | 0.933333333 | | Wake |
| 8 | 480 | 28800 | 8:00 AM | 0.875 | | Wake |
| 8.5 | 510 | 30600 | 8:30 AM | 0.823529412 | | Wake |
| 9 | 540 | 32400 | 9:00 AM | 0.777777778 | Normal TV off time | Wake |
| 9.5 | 570 | 34200 | 9:30 AM | 0.736842105 | | Wake |
| 10 | 600 | 36000 | 10:00 AM | 0.7 | | Wake |
| 10.5 | 630 | 37800 | 10:30 AM | 0.666666667 | | Wake |
| 11 | 660 | 39600 | 11:00 AM | 0.636363636 | Extra Ramp down time (Max) | Wake |
| 11.5 | 690 | 41400 | 11:30 AM | 0 | | |
| 12 | 720 | 43200 | 12:00 PM | 0 | | |
| 12.5 | 750 | 45000 | 12:30 PM | 0 | | |
| 13 | 780 | 46800 | 1:00 PM | 0 | | |
| 13.5 | 810 | 48600 | 1:30 PM | 0 | | |
| 14 | 840 | 50400 | 2:00 PM | 0 | | |
| 14.5 | 870 | 52200 | 2:30 PM | 0 | | |
| 15 | 900 | 54000 | 3:00 PM | 0 | | |
| 15.5 | 930 | 55800 | 3:30 PM | 0 | | |
| 16 | 960 | 57600 | 4:00 PM | 0 | | |
| 16.5 | 990 | 59400 | 4:30 PM | 0 | | |
| 17 | 1020 | 61200 | 5:00 PM | 0 | | |
| 17.5 | 1050 | 63000 | 5:30 PM | 0 | | |
| 18 | 1080 | 64800 | 6:00 PM | 0 | | |
| 18.5 | 1110 | 66600 | 6:30 PM | 0 | | |
| 19 | 1140 | 68400 | 7:00 PM | 0.863636364 | Normal Screen on time | Sleep |
| 19.5 | 1170 | 70200 | 7:30 PM | 0.886363636 | | Sleep |
| 20 | 1200 | 72000 | 8:00 PM | 0.909090909 | | Sleep |
| 20.5 | 1230 | 73800 | 8:30 PM | 0.931818182 | | Sleep |
| 21 | 1260 | 75600 | 9:00 PM | 0.954545455 | | Sleep |
| 21.5 | 1290 | 77400 | 9:30 PM | 0.977272727 | | Sleep |
| 22 | 1320 | 79200 | 10:00 PM | 1 | Normal TV off time ($T\_(S\_sec)$) | Sleep |
| 22.5 | 1350 | 81000 | 10:30 PM | 1.022727273 | | Sleep |
| 23 | 1380 | 82800 | 11:00 PM | 1.045454545 | | Sleep |
| 23.5 | 1410 | 84600 | 11:30 PM | 1.068181818 | | Sleep |
| 24 (0) | 1440 | 86400 | 12:00 AM | 1.090909091 | | Sleep |

ENHANCING USER SLEEP CYCLE

BACKGROUND

Since the advent of computer screens and displays, viewers of video content on computer screens and displays have been adversely impacted, most notably by the viewers experiencing less restful sleep due to viewing video content after the viewer's normal sleep time. Mammals are conditioned to associate blue light with morning and red light with evening. As such, reducing blue spectrum output and introducing more red spectrum can aid in sleep and prevent some of the negative effects of too much blue light being provided to a viewer of video content.

By exposing a viewer of video content with blue spectrum late at night, this may lead to difficultly in going to sleep and may lead to restless sleep by the viewer when the viewer eventually goes to sleep. Also, exposing the viewer with red spectrum when the user is awake during the middle of the day, for example, may lead to a less productive (e.g., drowsy) viewer wake state.

The disclosure described in detail below provides a solution to the problem associated with the hindrance of a sleep state or a wake state of a viewer of video content.

SUMMARY

This summary is not intended to identify critical or essential features of the disclosures herein, but instead merely summarizes certain features and variations thereof. Other details and features will also be described in the sections that follow.

Methods described herein may provide a viewer of video content with content comprising pixels that are color-shifted based on a time of day when the viewer is viewing the content. Studies have shown that the blue light spectrum prevents the body from producing melatonin, whereby an increase in melatonin is believed to trigger the circadian rhythms in the human body and causes humans to feel tired at night. According to the method described herein, when the time of day that the video content is viewed is around the viewer's normal sleep time, pixels are color shifted to increase a red color of the video content. When the time of day that the video content is viewed is around the viewer's normal wake time, pixels are color shifted to increase a blue color of the video content.

A method described herein may comprise receiving video content for display, determining a time of day the video content is to be displayed on a display screen, determining a time of day when a user viewing the video content is expected to go to sleep, and based on the time of day when the user is expected to go to sleep and based on a current time of day when the video content is being displayed on the display screen, applying a color shift to at least one of red, green and blue (R, G, B) color values for (R,G,B) display screens, (R,G,B,Y) values for (R,G,B,Y) display screens, or (R,G,B,W) values for (R,G,B,W) display screens, of each pixel of the video content to be displayed on the display screen.

In some embodiments, the determining the time of day when the user is expected to go to sleep is based on an alarm clock setting. In some embodiments, the predicting the time of day when the user goes to sleep is based on the time when sunset is to occur (e.g., three hours after sunset). In some embodiments, the predicting the time of day when the user goes to sleep is based on historical ON/OFF data of the display screen, which may include information as to the user's personal time. In some embodiments, the predicting the time of day when the user goes to sleep is based on information obtained from the user's home security system.

In some embodiments, the applying of a color shift may comprise increasing a level of red color of each pixel of the video content to be displayed, and decreasing a level of blue color of each pixel of the video content to be displayed.

In some embodiments, the color shifting can be done gradually to minimize eye strain on the user. This gradual shifting can be done, for example, by adjusting the color by some small amount every minute, starting 30 minutes before the user's expected sleep time.

In some embodiments, the applying of a color shift may comprise determining that the current time of day is within a predetermined amount of time prior to when the user is expected to go to sleep, linearly increasing, within a period of time, a level of red color of each pixel of the video content to be displayed, and linearly decreasing, within the period of time, a level of blue color of each pixel of the video content to be displayed.

In some embodiments, the linear increasing of a level of red color is performed at a rate of X pixel color amount per minute for each pixel of the video content to be displayed on a display screen. The linear decreasing of a level of blue color is performed at a rate of Y pixel color amount per minute for one or more pixels of the video content to be displayed on the display screen, where X and Y are positive integers. The display screen may comprise a television monitor or a computer monitor.

In some embodiments, the periods of time when the pixel color shifting is performed is based on data obtained from a user's habits, such as typical times of day when the user wakes up and goes to sleep. For example, a user who works the night shift may have pixel color shifting to hasten sleepiness when the user is watching television during daylight hours when the user typically sleeps.

A method to improve wake time of a user is similar to the discussions above for improving a sleep time of a user, but whereby for the wake time improvement, color shift of video content is provided to increase a blue color value of pixels making up the video content based on a user's wake time, so that when the user wakes up and watches video that slowly transitions toward a more blue color, the user is provided with video content that enhances the user's wake state.

By way of example, in a 24-bit RBG pixel color scheme, a color of each pixel element corresponding to a sub-pixel of that pixel element may be represented by a corresponding red, green and blue (R,G,B) value of from 0 to 255, in which a RGB for a pixel element is represented as one point in a 256×256×256 three-dimensional cube, and in which any visible color may be represented as a particular R,G,B value on the 256×256×256 three-dimensional cube. Continuing with this example, the amount of red (R) in a pixel may be represented by an eight bit value such as 01001000 (=72) or 0000001 (=1), the amount of green (G) in the pixel may be represented by another eight bit value such as 00001101 (=13) or 01000001 (=65), and the amount of blue (B) in the pixel may be represented by another eight bit value such as 01001111 (=79) or 11110000 (=240). When pixels are displayed on a display screen, each pixel may be displayed with an associated RGB color based on the 0☐255 R value, 0☐255 G value, and 0☐255 B value assigned to that pixel. For example, a pixel having a RGB32 value of {0,0,255} corresponds to a completely blue color pixel with no green or red color, whereas a pixel having a RGB32 value of {255,0,0} corresponds to a completely red color pixel with no green or blue color. In application, each pixel to be displayed on a display screen may be built by driving three small and very close but separated RGB light sources, with an intensity of R, G and B based on the particular RGB32 value associated with that pixel.

The foregoing methods and other methods described herein may be performed by a system, a computing device, a computer readable medium storing computer-executable instructions for performing the methods, and/or an apparatus having a processor and memory storing computer-executable instructions for performing the methods.

BRIEF DESCRIPTION OF THE DRAWINGS

Some features herein are illustrated by way of example, and not by way of limitation, in the figures of the accompanying drawings and in which like reference numerals refer to similar elements.

FIG. 16 is a flow diagram showing different types of pixel color shifting that may be performed, according to one or more illustrative aspects of the disclosure.

FIG. 17 is a table showing a first example in which red, green and blue color values of a pixel are color-shifted over time to enhance sleepiness, according to one or more illustrative aspects of the disclosure.

FIG. 19 is a table showing a second example in which red, green and blue color values of a pixel are color-shifted over time to enhance sleepiness, according to one or more illustrative aspects of the disclosure.

FIG. 21 is a table of an example in which pixel color-shifting sleep time periods and the pixel color-shifting wake time periods are provided at different times within a 24 hour day, according to one or more illustrative aspects of the disclosure.

DETAILED DESCRIPTION

Figure 1:
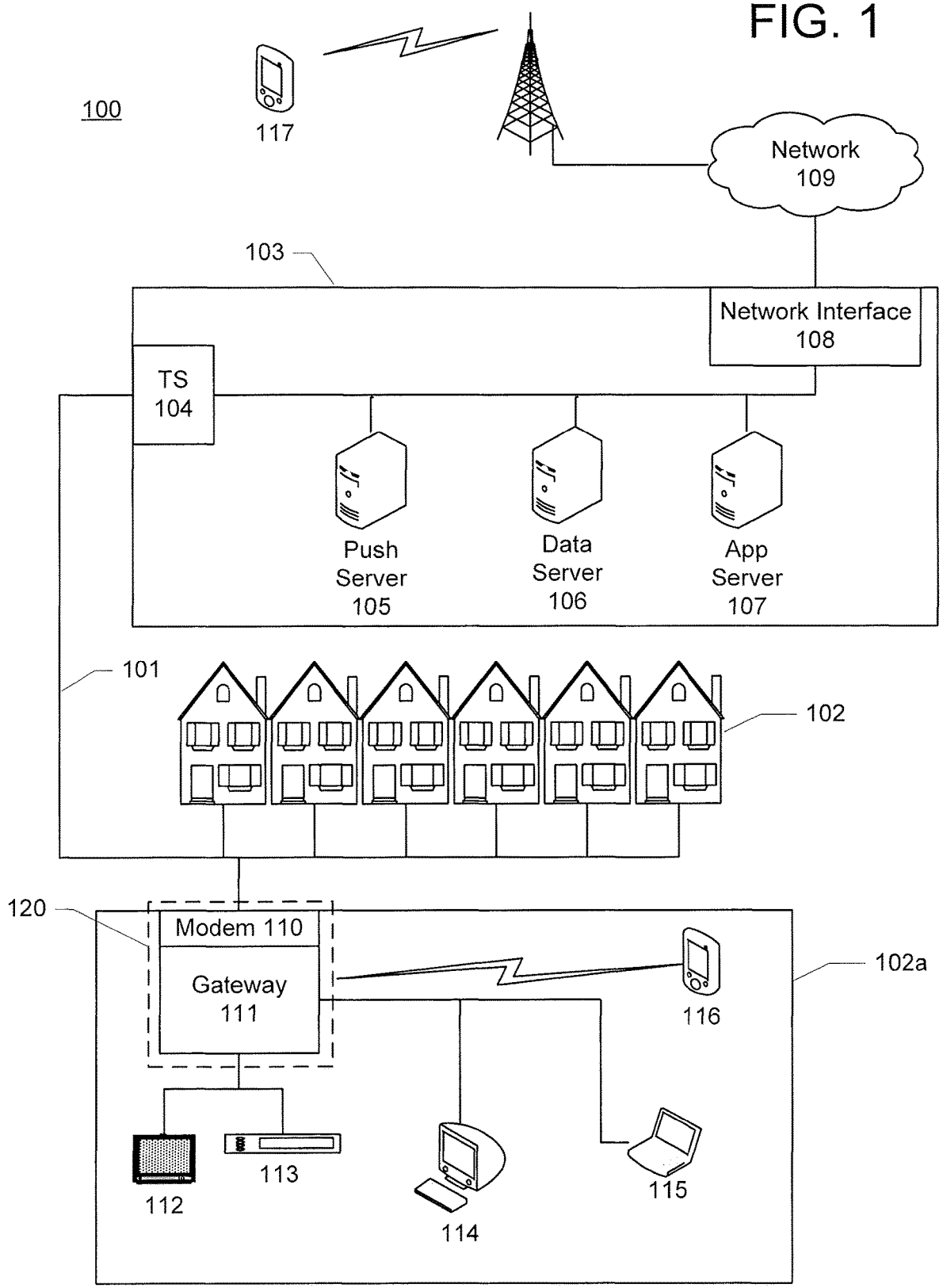
FIG. 1 illustrates an example information access and distribution network.

FIG. 1 illustrates an example information access and distribution network 100 on which many of the various features described herein may be implemented. The network 100 may be any type of information distribution network, such as satellite, telephone, cellular, wireless, etc. One example may be an optical fiber network, a coaxial cable network or a hybrid fiber/coax (HFC) distribution network. Such networks 100 use a series of interconnected communication links 101 (e.g., coaxial cables, optical fibers, wireless connections, etc.) to connect multiple premises, such as locations 102 (e.g., homes, businesses, institutions, etc.), to a local office 103 (e.g., a central office or headend). The local office 103 may transmit downstream information signals onto the links 101, and each location 102 may have a receiver used to receive and process those signals.

There may be one link 101 originating from the local office 103, and it may be split a number of times to distribute the signal to various locations 102 in the vicinity (which may be many miles) of the local office 103. Although the term home is used by way of example, locations 102 may be any type of user premises, such as businesses, institutions, etc. The links 101 may include components not illustrated, such as splitters, filters, amplifiers, etc. to help convey the signal clearly. Portions of the links 101 may also be implemented with fiber-optic cable, while other portions may be implemented with coaxial cable, other links, or wireless communication paths.

The local office 103 may include an interface 104, which may be a termination system (TS), such as a cable modem termination system (CMTS), which may be a computing device configured to manage communications between devices on the network of links 101 and backend devices such as servers 105-107 (to be discussed further below). The interface 104 may be as specified in a standard, such as, in an example of an HFC-type network, the Data Over Cable Service Interface Specification (DOC SIS) standard, published by Cable Television Laboratories, Inc. (a.k.a. Cable-Labs), or it may be a similar or modified device instead. The interface 104 may be configured to place data on one or more downstream channels or frequencies to be received by devices, such as modems at the various locations 102, and to receive upstream communications from those modems on one or more upstream frequencies. The local office 103 may also include one or more network interfaces 108, which can permit the local office 103 to communicate with various other external networks 109. These networks 109 may include, for example, networks of Internet devices, telephone networks, cellular telephone networks, fiber optic networks, local wireless networks (e.g., WiMAX), satellite networks, and any other desired network, and the network interface 108 may include the corresponding circuitry needed to communicate on the network 109, and to other devices on the network such as a cellular telephone network and its corresponding cell phones (e.g., cell phone 117).

As noted above, the local office 103 may include a variety of servers 105-107 that may be configured to perform various functions. For example, the local office 103 may include a push notification server 105. The push notification server 105 may generate push notifications to deliver data and/or commands to the various locations 102 in the network (or more specifically, to the devices in the locations 102 that are configured to detect such notifications). The local office 103 may also include a data server 106. The data server 106 may be one or more computing devices that are configured to provide data to users in the homes. This data may be, for example, video on demand movies, television programs, songs, text listings, etc. The data server 106 may include software to validate user identities and entitlements, locate and retrieve requested data, encrypt the data, and initiate delivery (e.g., streaming) of the data to the requesting user and/or device.

The local office 103 may also include one or more application servers 107. An application server 107 may be a computing device configured to offer any desired service, and may run various languages and operating systems (e.g., servlets and JSP pages running on Tomcat/MySQL, OSX, BSD, Ubuntu, Redhat, HTML5, JavaScript, AJAX and COMET). For example, an application server may be responsible for collecting data such as television program listings information and generating a data download for electronic program guide listings. Another application server may be responsible for monitoring user viewing habits and collecting that information for use in selecting advertisements. Another application server may be responsible for formatting and inserting advertisements in a video stream being transmitted to the locations 102.

An example location 102a may include an interface 120. The interface may comprise a device 110, such as a modem, which may include transmitters and receivers used to communicate on the links 101 and with the local office 103. The device 110 may be, for example, a coaxial cable modem (for coaxial cable links 101), a fiber interface node (for fiber optic links 101), or any other desired modem device. The device 110 may be connected to, or be a part of, a gateway 111 (e.g., a gateway interface device). The gateway 111 may be a computing device that communicates with the device 110 to allow one or more other devices in the home to communicate with the local office 103 and other devices beyond the local office. The gateway 111 may be a set-top box (STB), digital video recorder (DVR), computer server, or any other desired computing device. The gateway 111 may also include (not shown) local network interfaces to provide communication signals to devices in the home, such as televisions 112, additional STBs 113, personal computers 114, laptop computers 115, wireless devices 116 (wireless laptops and netbooks, mobile phones, mobile televisions, personal digital assistants (PDA), etc.), and any other desired devices. Examples of the local network interfaces include Multimedia Over Coax Alliance (MoCA) interfaces, Ethernet interfaces, universal serial bus (USB) interfaces, wireless interfaces (e.g., IEEE 802.11), Bluetooth interfaces, and others.

Figure 2:
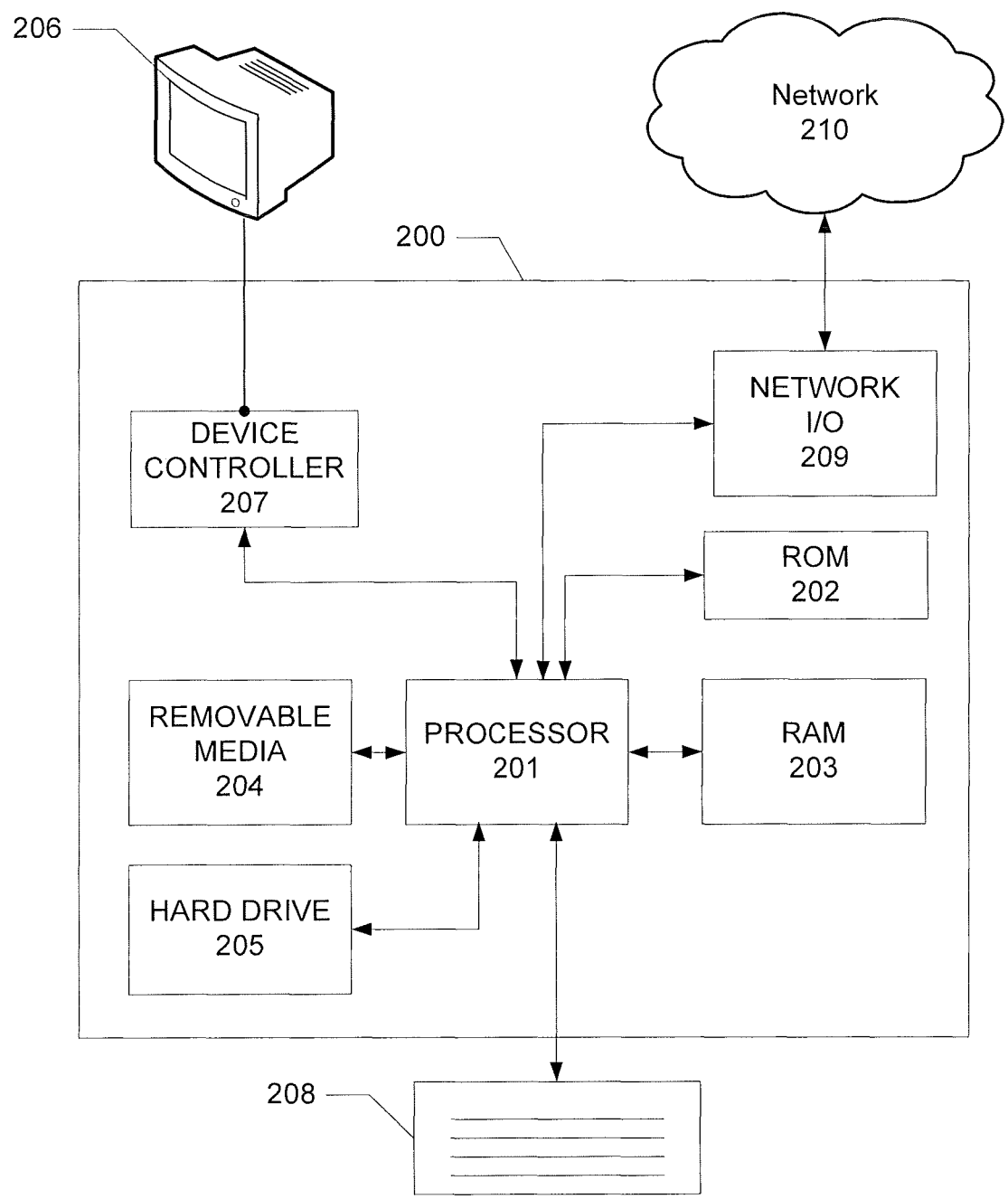
FIG. 2 illustrates an example hardware and software platform on which various elements described herein can be implemented.

FIG. 2 illustrates general hardware and software elements that can be used to implement any of the various computing devices (e.g., terminal devices, remote control devices, etc.) discussed herein. The computing device 200 may include one or more processors 201, which may execute instructions of a computer program to perform any of the features described herein. The instructions may be stored in any type of computer-readable medium or memory, to configure the operation of the processor 201. For example, instructions may be stored in a read-only memory (ROM) 202, random access memory (RAM) 203, hard drive, removable media 204, such as a Universal Serial Bus (USB) drive, compact disk (CD) or digital versatile disk (DVD), floppy disk drive, or any other desired electronic storage medium. Instructions may also be stored in an attached (or internal) hard drive 205. The computing device 200 may include one or more output devices, such as a display 206 (or an external television), and may include one or more output device controllers 207, such as a video processor. There may also be one or more user input devices 208, such as a remote control, keyboard, mouse, touch screen, microphone, etc.

The computing device 200 may also include one or more network interfaces 209, such as input/output circuits (such as a network card) to communicate with an external network 210. The interface 209 may be a wired interface, wireless interface, or a combination of the two. In some embodiments, the interface 209 may include a modem (e.g., a cable modem), and the network 210 may include the communication links 101 discussed above, the external network 109, an in-home network, a provider's wireless, coaxial, fiber, or hybrid fiber/coaxial distribution system (e.g., a DOCSIS network), or any other desired network. The computing device 200 may communicate with the external networks 210 or other devices using one or more communication protocols, such as wired communication protocols and wireless communication protocols (e.g., Wi-Fi, Bluetooth, Zig-Bee, Z-Wave, etc.).

Figure 3:
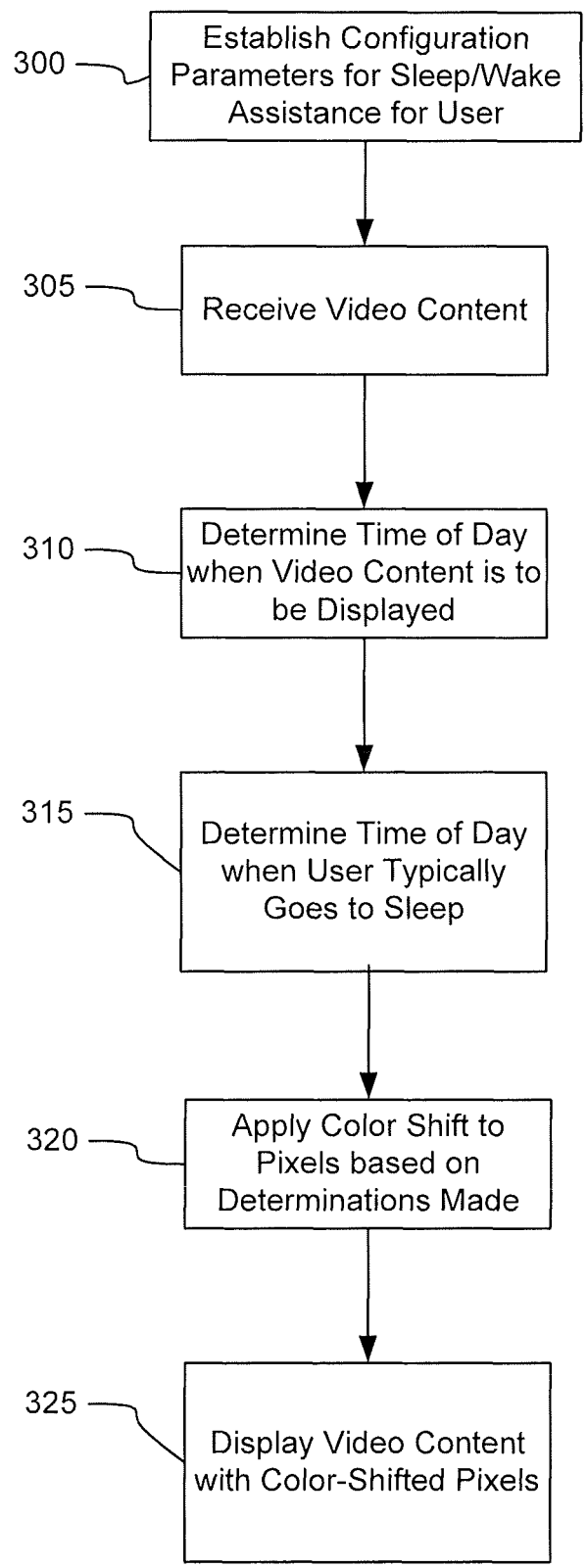
FIG. 3 illustrates an example summary of a method of displaying video content according to one or more illustrative aspects of the disclosure.

FIG. 3 illustrates an example summary of a method of displaying video content to a user according to one or more illustrative aspects of the disclosure. The steps may be performed by one or more computing device (such as, with reference to FIG. 1, a component at the location 102a such as set-top-box (STB) 113, a component (e.g., a computer, or server) at the local office 103, and/or a remote device that can communicate with the location 102a or the local office 103).

In step 300, configuration parameters for sleep and/or wake assistance to a user watching video content are established. This may be done, for example, by obtaining historical data regarding normal sleep times for a user based on times when the user's television is turned ON and turned OFF, and/or by obtaining sunrise and sunset times based on the day of the year and location of the user, and/or by obtaining home security data for a user's home to determine a time a user typically wakes up and typically goes to sleep (to be explained in more detail below with respect to one or more embodiments), and/or by receiving user input regarding a user's typical wake time and sleep time.

In step 305, video content is received. The video content may be received, for example, for display on a display screen. By way of example, the display screen may correspond to a television display, a personal computer display, a laptop computer display, a computer tablet display, or a smart phone display. For example, the display screen may be associated with computer 114 or 115 connected to STB 113, or the display screen may be associated with television 112 connected to STB 113. By way of example, video content may be received by STB 113 as shown in FIG. 1, as provided by data server 106. In some embodiments, the video content may be an on-demand video program, such as a movie, or playback of content previously recorded on a digital video recorder associated with the STB 113, or content currently being transmitted by a content providing service such as HBO□ or ESPN□.

In step 310, a time of day at which the video content is to be displayed on the display screen is determined. By way of example, the time of day may be determined by STB 113 based on reference to a clock associated with a computer associated with the STB 113, or by reference to information obtained from a network such as the Internet, a WAN or a LAN.

In step 315, a time of day when the user typically goes to sleep is determined. In some embodiments, this may be determined based on historical data regarding normal sleep times for a user based on times when the user's television is turned ON and turned OFF. In some embodiments, the time of day when the user typically goes to sleep may be determined based on the user's home security system which indicates when the user's home is placed in a high security mode signifying a time of day when the user goes to sleep. In some embodiments, the time of day when the user typically goes to sleep may be determined based on when sunset is to occur on the day when the video content is to be displayed as a frame of data on the display screen is determined. By way of example, the time of day when sunset is to occur may be determined by STB 113 based on reference to information obtained from a network such as the Internet, which is accessible by a computer associated with the STB 113, or based on information stored in a memory of the STB 113 regarding sunset times associated with each day of the year. In step 320, based on the time of day when the user typically goes to sleep and a current time of day when the video content is being displayed as a frame of data on the display screen, a color shift is applied to at least one of red, green and blue (R, G, B) color values of at least one pixel of the video content to be displayed on the display screen. The color shifting of a pixel may be considered to be a phase shift of the pixel's (R, G, B) color value, for example. By way of example, STB 113 applies a color shift to at least one of red, green and blue (R, G, B) color values of each pixel of the video content to be displayed on the display screen of television 112, based on a difference between the time of day when sunset is to occur and the current time of day when the video content is being displayed as a frame of data on the display screen of the television 112. See, for example, the color shifting of pixel 58 shown in FIG. 5 and FIG. 6, which increases the red color content of that pixel slowly and that decreases the blue color content of that pixel slowly over a period of time based on the user's predicted sleep time. In another example, STB 113 applies a color shift to at least one of red, green and blue (R, G, B) color values of each pixel of the video content to be displayed on the display screen of television 112, based on a difference between the current time of day and the predicted sleep time of the user, in which the predicted sleep time of the user is obtained based on historical data regarding normal sleep times for a user based on times when the user's television is turned ON and turned OFF. In yet another example, STB 113 applies a color shift to at least one of red, green and blue (R, G, B) color values of each pixel of the video content to be displayed on the display screen of television 112, based on a difference between the current time of day and the predicted sleep time of the user, in which the predicted sleep time of the user is obtained based on data obtained from a user's home security system that indicates when the user's home is placed in a high security mode (e.g., a security mode that has an in-house motion detection device enabled) signifying a time when the user goes to sleep. Further details of the amount and the rate of color shifting that may be applied to pixels to be displayed to a user are described below, such as with reference to FIGS. 5, 6 and 17-20.

In step 325, video content with color-shifted pixels as determined in step 320 is output to the display screen, for display to a user.

Figure 4:
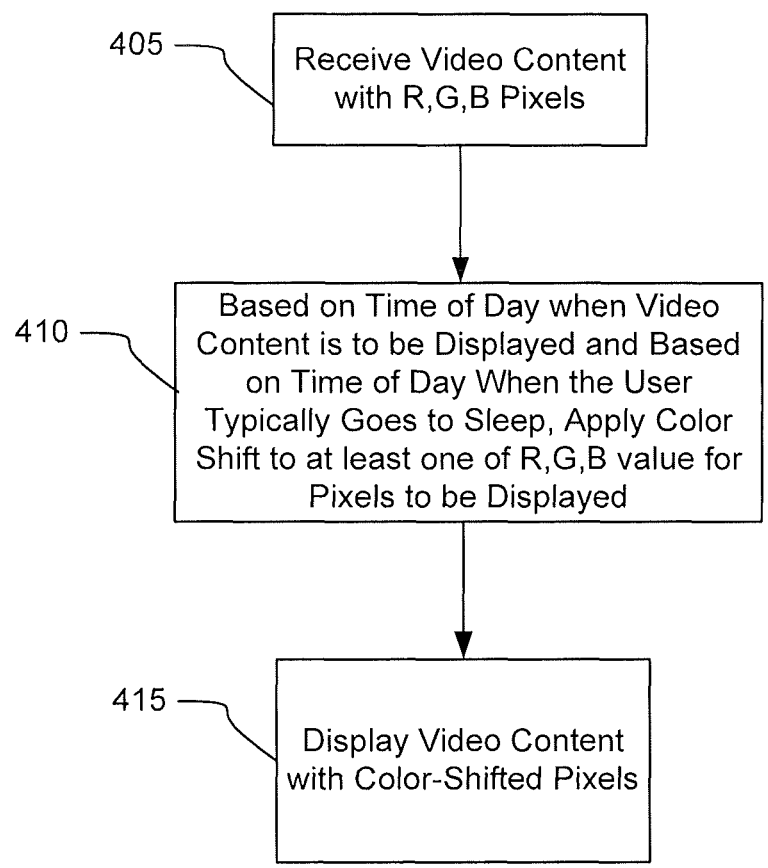
FIG. 4 illustrates an example method in which color values associated with pixels of video content to be displayed on a display screen are color shifted, according to one or more illustrative aspects of the disclosure.

FIG. 4 illustrates an embodiment in which color values associated with pixels of video content to be displayed on a display screen are color shifted, with reference to a RGB32 pixel color scheme.

In a RGB32 pixel color scheme, a color of each pixel element may be represented by a value of from 0 to 255, in which a RGB for a pixel element is represented as one point in a 256×256×256 three-dimensional cube. Continuing with this example, the amount of red (R) in a pixel may be represented by an eight bit value such as 01001000 (=72) or 0000001 (=1), the amount of green (G) in the pixel may be represented by another eight bit value such as 00001101 (=13) or 01000001 (=65), and the amount of blue (B) in the pixel may be represented by another eight bit value such as 01001111 (=79) or 11110000 (=240). When pixels are displayed on a display screen, each pixel is displayed with an associated RGB color based on the 0□255 R value, 0□255 G value, and 0□255 B value assigned to that pixel. For example, a pixel having a RGB32 value of {0,0,255} corresponds to a completely blue color pixel with no green or red color, whereas a pixel having a RGB32 value of {255,0,0} corresponds to a completely red color pixel with no green or blue color. In application, each pixel displayed on a display screen may be built by driving three small and very close but separated RGB light sources that provide an R sub-pixel, G sub-pixel and B sub-pixel component of each pixel, with an intensity of R, G and B based on the particular RGB32 value associated with that pixel.

In step 405, video content is received. For example, the video content may be output from data server 106 to STB 113 as shown in FIG. 1, for display on a display screen. Each pixel of the video content has an associated RGB32 value, such as {13,165,210} for pixel #58 of a 1080 pixel grid array to be displayed in each frame of video content to be displayed on a display of television 112.

In step 410, based on the time of day when the user typically goes to sleep and a current time of day when the video content is being displayed on the display screen, a color shift is applied to at least one of red, green and blue (R, G, B) color values of each pixel of the video content to be displayed on the display screen. By way of example, if the current time of day is 30 minutes before the user typically goes to sleep, then a color shift is applied to each pixel such that the B color value of each pixel of the video content to be displayed within a frame of video on the display screen of the television 112 is lowered by one (1) for each minute after the □30 minutes before sleep□time the frame of video that includes those pixels is displayed. In the example provided above with three small and very close but separated RGB light sources providing the light components for pixels making up a frame of video data to be displayed, the red color value for each pixel may be increased by increasing a power output of the red (R) light source, and the blue color value for each pixel may be decreased by decreasing a power output of the blue (B) light source. The pixel color shift adjustment may be performed as long as the television is turned on during a time period associated with a normal sleep time of the user.

In step 415, the video content is displayed with the color-shifted pixels.

Figure 5:
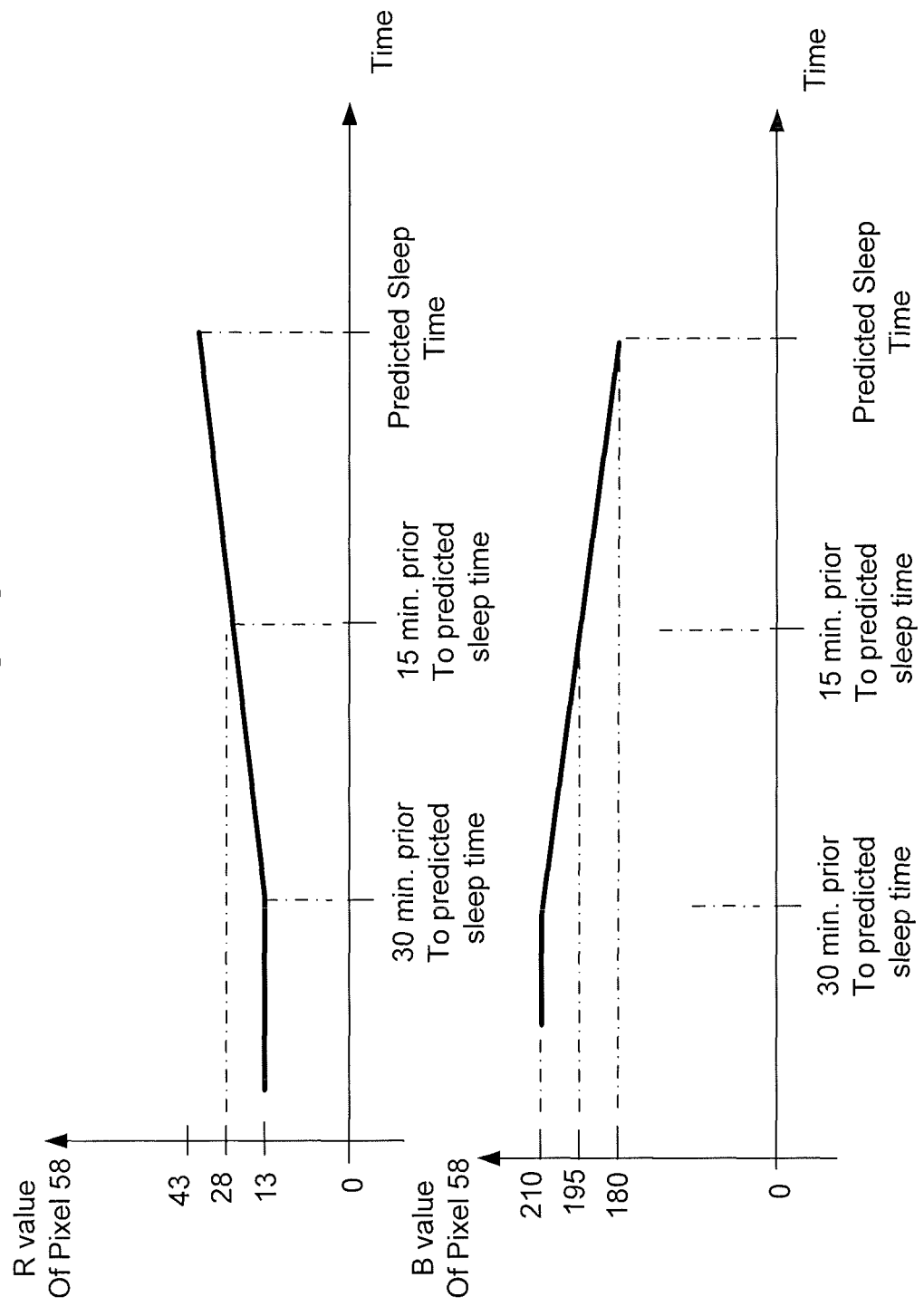
FIG. 5 shows an example of how red and blue pixel values are color shifted to act as a sleep aid, according to one or more illustrative aspects of the disclosure.

FIG. 5 shows an example of how pixel values may be color shifted, according to an embodiment that estimates the user's typical sleep time based on the time of day when sunset is to occur. In this example, color shifting of pixels is started at 30 minutes prior to sunset, and continued up to and after sunset. The color shifting is performed in an amount corresponding to 1 pixel color value per minute for every minute after 30 minutes prior to sunset in this example. Pixel #58 of a 1080 pixel grid array has a RGB32 value of {13,165,210}, and is received from data server 106 at a time corresponding to 30 minutes before sunset. Since the time at which Pixel #58 is to be displayed (along with other pixels) on a screen of television 112 is close to sunset, the RGB values of Pixel #58 are color shifted to {13+1=14, 165, 210−1=209}, and displayed with the other 1079 pixels of a frame of video on the screen of television 112.

At a time corresponding to 29 minutes before sunset, Pixel #5 is received from data server 106 with a RGB32 value of {13,165,210}, the same as its value at the time corresponding to 30 minutes before sunset. Since the time at which Pixel #58 is to be displayed (along with other pixels) on a screen of television 112 is now one minute closer to sunset, the RGB values of Pixel #58 are color shifted to {13+2=15, 165, 210−2=208}, and displayed with the other 1079 pixels of a frame of video on the screen of television 112.

In a similar manner, at a time corresponding to 15 minutes before sunset, Pixel #58 is received from data server 106 with a RGB32 value of {13,165,210}, the same as its value at the time corresponding to 30 minutes and 29 minutes before sunset. Since the time at which Pixel #58 is to be displayed (along with other pixels) on a screen of television 112 is now much closer to sunset, the RGB values of Pixel #58 are color shifted to {13+15=28, 165, 210−15=195}, and displayed with the other 1079 pixels of a frame of video on the screen of television 112.

In the example of FIG. 5, the color-shifting of pixels to be displayed is done in a linear manner, based on a time when the video content is to be displayed on a display, as compared to a time when sunset occurs on that day. In more detail, in the example of FIG. 5, the red pixel color value is color-shifted from a value X to a value □X+(time difference between when pixel is to be displayed and 30 minutes prior to sunset time), when the time when the pixel is to be displayed is after 30 minutes prior to sunset time. If the time when the pixel is to be displayed is prior to 30 minutes prior to sunset time for that day, then no color-shifting is performed on that pixel. Continuing with this example, if the sunset time is 5:16 p.m., and the time when pixel is to be displayed on a display screen is 5:21 p.m., and the red pixel color value X of Pixel #58 is equal to 78, then the red pixel color value X of Pixel #58 is color-shifted to 78+|(4:50 p.m.)□(5:21 p.m.)|=78+31=109. If the color-shifting is computed such that the red pixel color value X is to be changed to a value above 255, then the color-shifting is made such that the red pixel color value X is maintained at 255 for that pixel.

Figure 6:
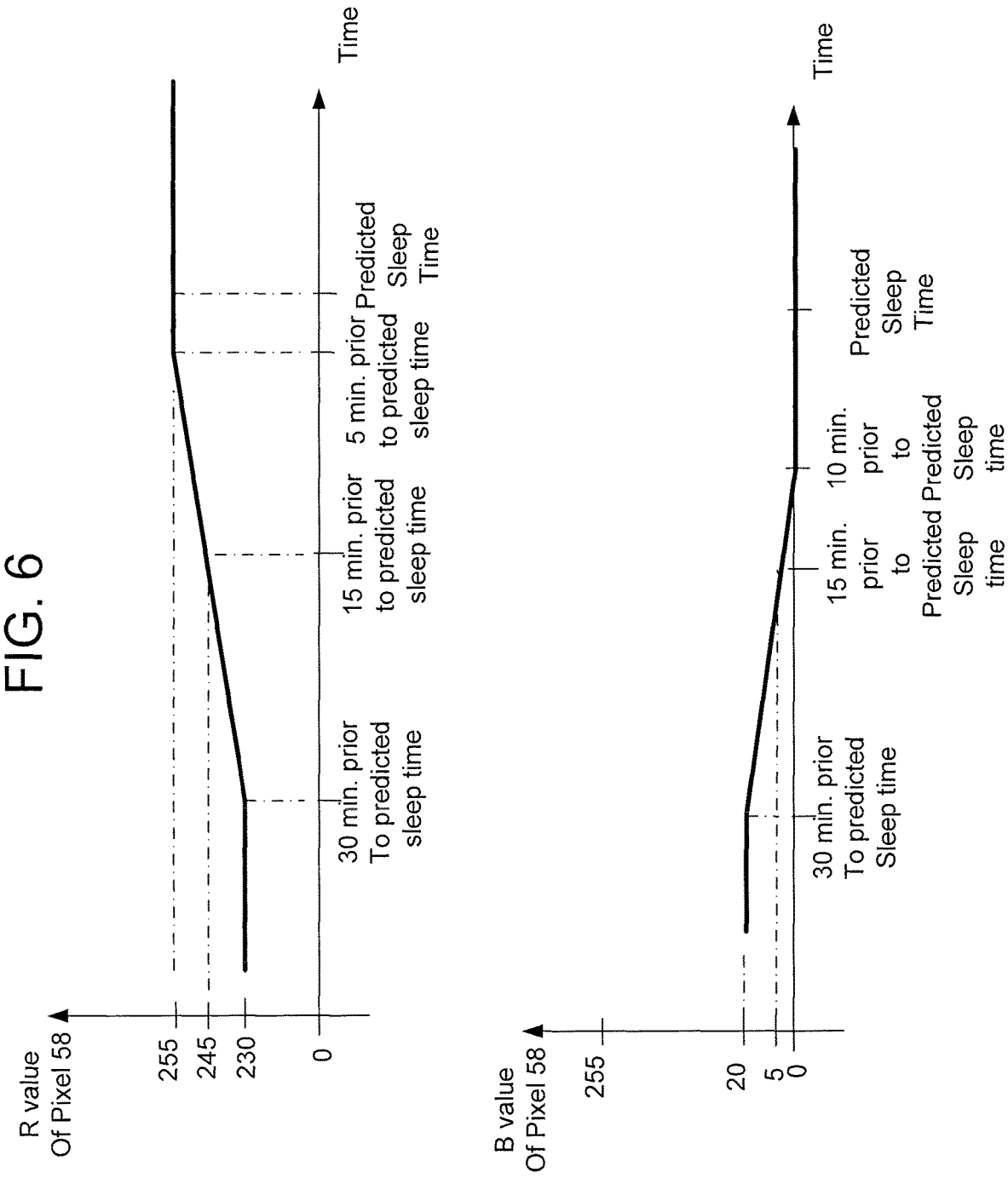
FIG. 6 shows another example of how red and blue pixel values are color shifted to act as a sleep aid, according to one or more illustrative aspects of the disclosure.

FIG. 6 illustrates an example where the red pixel color value of Pixel 58 is increased to the maximum value of 255 at 5 minutes prior to sunset and maintained at that maximum red color value up until the television is turned OFF.

In a similar manner, referring again to FIG. 5, the blue pixel color value is color-shifted from a value Y to a value □Y−(time difference between when pixel is to be displayed and 30 minutes prior to the user's predicted sleep time)□, when the time when the pixel is to be displayed is after 30 minutes prior to the user's predicted sleep time. If the time when the pixel is to be displayed is prior to 30 minutes prior to the user's predicted sleep time, then no color-shifting is performed on that pixel. Continuing with this example, if the sunset time is 5:16 p.m., and the time when pixel is to be displayed on a display screen is 5:27 p.m., and the blue pixel color value Y of Pixel #58 is 198, then the blue pixel color value Y of Pixel #58 is color-shifted to 198−|(4:50 p.m.)□(5:27 p.m.)|=198−37=161. If the color-shifting is computed such that the blue pixel color value Y is to be changed to a value less than zero (0), then the color-shifting is made such that the blue pixel color value Y is maintained at zero (0) for that pixel. FIG. 6 shows a case where the blue pixel color value of Pixel #58 is decreased to the minimum value of 0 at 10 minutes prior to sunset and maintained at that minimum blue color value up until the television is turned OFF.

In some embodiments, a sunset time may be used to predict the time for that day when a user goes to sleep (e.g., the user's predicted sleep time is determined to be 3 hours after the sunset time for that day). In other embodiments, actual usage data may be obtained for a television within a home, and based on the actual usage data, predictions may be made (such as by a controller housed within a STB) as to what time a user typically turns off the television in the evening, and that time may be used to gradually shift the pixel colors. For example, if actual usage data for a television in a user's bedroom indicates that the television set has been turned off at 9:30 p.m., 9:15 p.m., 10 p.m., and 8:45 p.m. in the last four days, respectively, then an average of those four values can be computed, and used to predict a time when the user will turn off the television on the current day. Based on the example values provided above, the predicted time that a user will turn off his/her television is computed to be (9.5+9.25+10+8.75)/4=9:22 p.m. Based on the predicted television OFF time of 9:22 p.m., then the pixel color values may be color shifted starting at 30 minutes before the predicted television OFF time, which corresponds in this example to 8:52 p.m. The color shifting may be performed linearly up to 9:22 p.m., at which time the television screen stays at a red-shifted pixel color for each pixel to be displayed, until the television is actually turned OFF and the user goes to bed.

By way of example, the red value for each pixel in a frame of data displayed on the display screen may be color-shifted 'upward' by an amount equal to a value of 2 starting at 8:52 p.m., and increased by an amount equal to a value of 2 for each minute up to 9:22 p.m. (unless the pixel value of a pixel is at the value 255, whereby it is maintained at that value until the television is turned OFF). At the same time, the blue value for each pixel in in a frame of data displayed on the display screen may be color-shifted 'downward' by an amount equal to a value of 2 starting at 8:52 p.m., and decreased by amount equal to a value of 2 for each minute up to 9:22 p.m. (unless the pixel value of a pixel is at the value 0, whereby it is maintained at that value until the television is turned OFF)

In some embodiments, a prediction may be made (such as by a controller housed within a STB) as to what time a user typically turns off the television on a particular day of the week during the evening of that particular day, and that time may be used to gradually shift the pixel colors.

Figure 7:
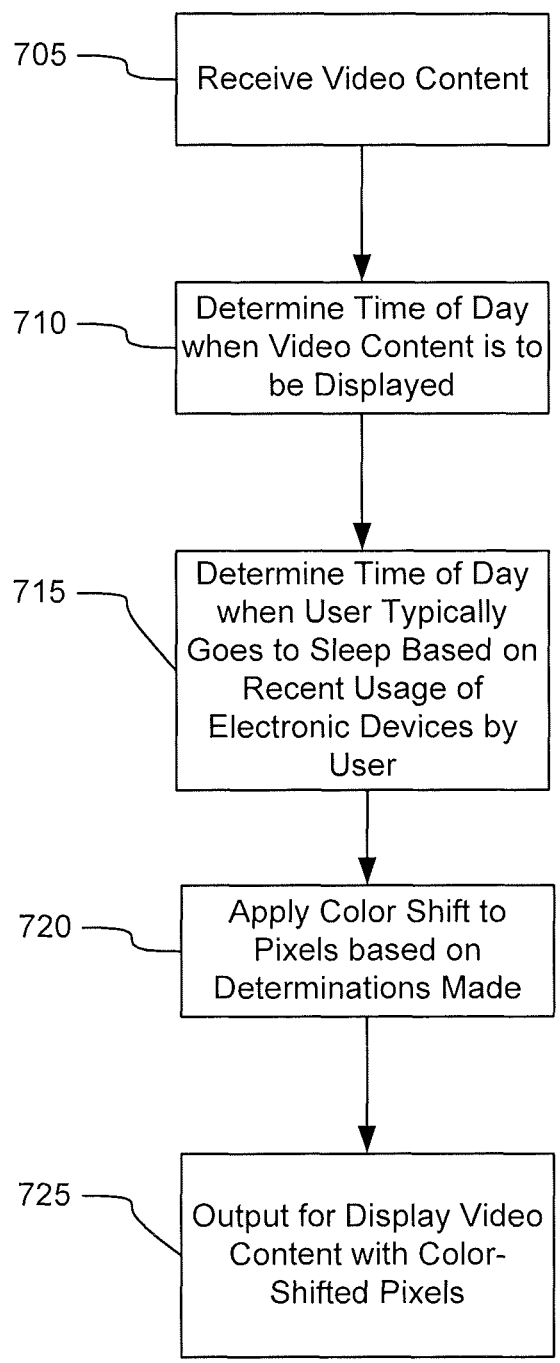
FIG. 7 is a flow diagram describing a pixel color shifting process, according to one or more illustrative aspects of the disclosure.

FIG. 7 is a flow diagram of a method of modifying video content based on recent television usage, according to an embodiment, whereby FIG. 7 differs from FIG. 3 in that recent usage of electronic devices (e.g., usage of smart phone, tablet, PC, etc.) of a user are utilized to determine a time of day when the user typically goes to sleep. In step 705, video content is received. For example, the video content may be received for display on a computer display or television or smart phone. In step 710, a time of day when the received video content is to be displayed is determined. In step 715, a time of day when the user associated with computer or television or smart phone typically goes to sleep is determined, based on recent usage of electronic devices by the user (e.g., times when a computer, television, and/or smart phone is turned OFF from an ON state). In step 720, a color shift is applied to pixels to be displayed in a frame of video content on the computer display or television or smart phone based on the determined time of day when the video content is displayed, as compared to the time of day when the user associated with the computer or television or smart phone typically goes to sleep. In step 725, the color-shifted video content is output for display by the computer or television or smart phone.

In some embodiments, a prediction may be made as to what time a user will likely turn off the television based on home security data, such as a home security system that is programmed by the user. For example, if the user has programmed his/her home security system to go from a □normal□mode to a □high alert□mode that may be used when the user goes to bed, then the time when the home security system goes to the high alert mode may be used as predicted time when the television is turned OFF. The normal mode may be a mode where only perimeter alarms, such as door and window alarms, are activated, and the □high alert□mode may be a mode in which motion sensors within the user's home are also activated (since the user is likely in bed and thus any motion detected by the motion sensors is from an unauthorized person within the user's home). The use of home security data provides useful information regarding when a person in that home typically goes to bed to sleep and gets out of bed after sleeping, to be used to customize a pixel color shifting wake time period and a pixel color shifting sleep time period for persons living in that home.

By way of example, if a user has programmed his/her home security system to transition from a normal mode to a high alert mode at 11 p.m. on a particular day, then the 11 p.m. time may be used as the predicted time when the user will be turning OFF his/her television on that day, and whereby red and blue pixel values of pixels to be displayed within a frame of video by the television are color shifted in accordance with the current time when the frame of video is displayed and the predicted time when the television is to be turned OFF. In this embodiment, the predicted time when the user will be turning OFF the television may be obtained from the home security system data, and may be used to determine when to color shift pixels to be displayed by the television to increase the red level of pixels and decrease the blue level of pixels to be displayed, and not based on the time when sunset is to occur in a region where the user is located. For example, if the sunset time for a particular day is 8:00 p.m., but the home security system data is such that the security mode is to transition from normal mode to high alert mode at 11 p.m., the 11 p.m. 'home security data' time and not the 8:00 p.m. 'sunset' time may be used to set the time period for performing color shifting of pixels to increase sleepiness of a user watching video content.

Also, by way of example, if a user has programmed his/her home security system to transition from a normal mode to a high alert mode at 7 a.m. on a particular day, then the 7 a.m. time may be used as the predicted time when the user will be turning OFF his/her television in the morning and leave the home to go to work (since any movement in the home when the user has left for work detected to a motion sensor activated when the security system is in the high alert mode is likely due to an intruder), and whereby red and blue pixel values of pixels to be displayed within a frame of video by the television are color shifted in accordance with the current time when the frame of video is displayed and the predicted time when the television is to be turned OFF. In this embodiment, the predicted time when the user will be turning OFF the television in the morning may be used to determine when to color shift pixels to be displayed by the television to increase the blue level of pixels and decrease the red level of pixels to be displayed, and not the time when sunrise is to occur in a region where the user is located.

In some embodiments, the device lights of the STB 113 co-located with the television 112 may also color shifted in the same manner as the pixels comprising the video content to be displayed by the television 112, to provide an even more light-friendly environment to enable a user to be more inclined to go to sleep soon after the user turns off the television 112. Those device lights of the STB 113 may include a POWER ON light, lights showing the current television channel being viewed by the user (e.g., □355□, and lights indicating the current time of day (e.g., 10:57 p.m.).

In some embodiments, the color shifting of pixels on a television may be used as a form of parental control of television use, whereby the video content displayed on the television screen may be modified so as to make a minor child watching television during the evening more likely to become sleepy and want to go to bed, as opposed to staying up late and being too tired the next morning to function well at school. In other embodiments, while a minor child is watching television in the morning, such as while eating his/her breakfast, color shifting of pixels displayed on a television screen may be performed so as to increase the blue color of pixels and decrease the red color of pixels, to thereby assist the minor child to be in an awake state prior to leaving the home to go to school. The determination of which television set in a home is associated with a child may be based on the room within the home that the television set is located (e.g., within the child's room), or may be based on settings created based on a user profile (e.g., television #1 associated with a teenage child, television 2 associated with a pre-school child, etc.).

In some embodiments, the color shifting of pixels provided within a frame of video content displayed on a television or computer display may be controlled by a STB that controls a television and that utilizes HDMI (High-Definition Multimedia Interface) protocols and HDMI signaling to effect such color shifting of pixels. HDMI is a well known audio/video interface for transferring uncompressed video data and compressed or uncompressed digital audio data from an HDMI-compliant source device, such as a display controller, to a compatible computer monitor, video projector, digital television, or digital audio device. In other embodiments, the ability to disable the color shifting of pixels may be via a user selection on a remote control device, whereby a user may choose to watch television without any modification of the pixels displayed by the television in the manner as described hereinabove with respect to different embodiments.

In some embodiments, the user may have an option to either allow the color shifting of pixels to occur automatically whenever the television or computer display is turned on, or to instead make an affirmative selection to turn on the color shifting of pixels feature each time the television or computer display is turned on. By way of example, in the latter case, the user may go into the □Settings□menu of a television programming device (e.g., STB), and select □Turn Pixel Color Shifting Feature ON□via a remote control device, in order to adjust the pixel colors in the manner as described above. Alternatively, with the color shifting feature previously turned ON, the use may go into the □Settings□menu and select □Turn Pixel Color Shifting Feature OFF□via the remote control device.

Figure 8:
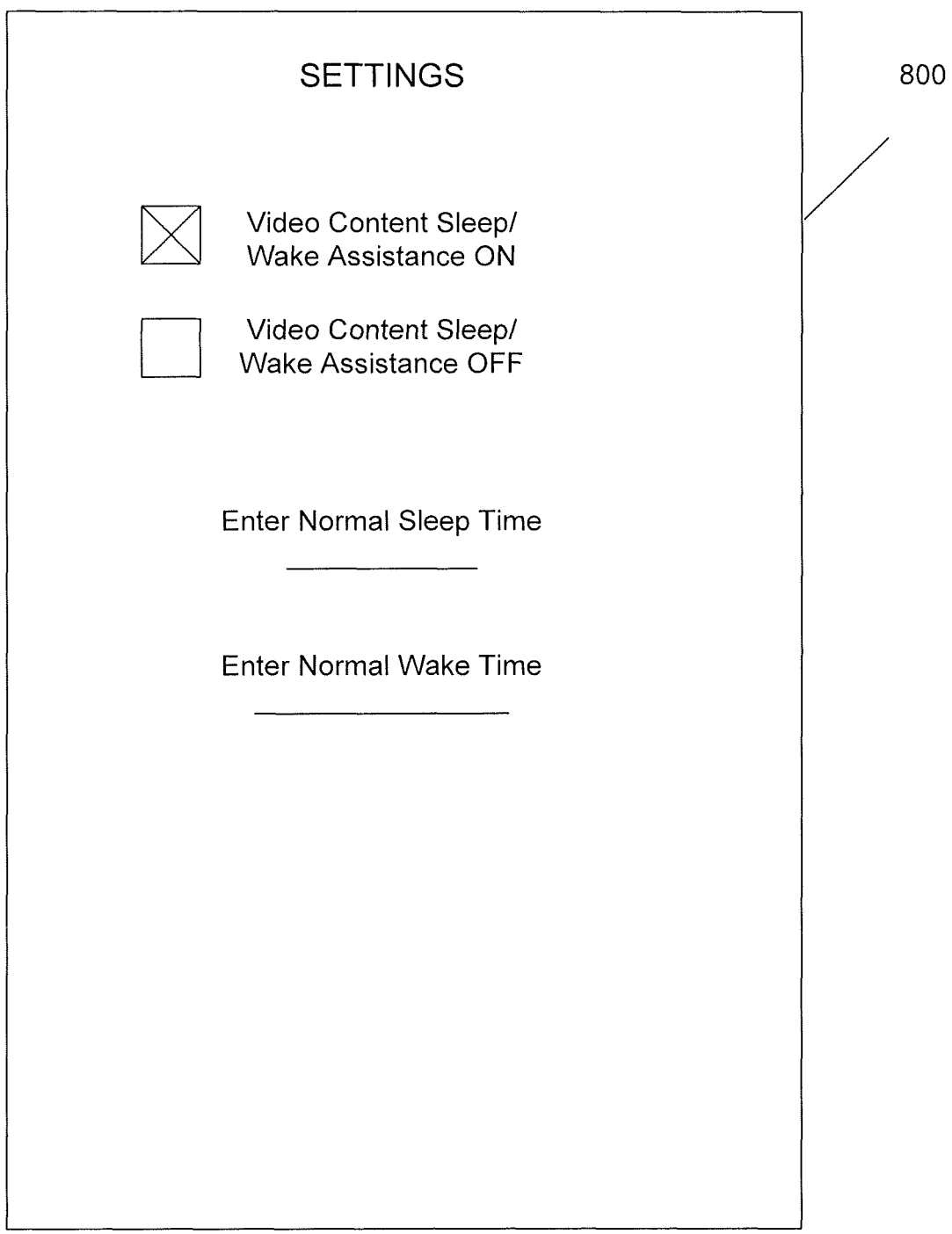
FIG. 8 shows one possible implementation of a settings menu accessible by a user's television remote control unit, according to one or more illustrative aspects of the disclosure.

FIG. 8 shows one possible implementation of a settings menu 800 accessible by a user's television remote control unit or via buttons on the user's television set. When the user enters the settings menu 800, the user is provided with an option to either turn ON video content sleep/wake assistance, or turn OFF video content sleep/wake assistance. Additionally, the user may provide information on the settings menu 800 regarding the user's normal sleep time and the user's normal wake time, to be used to determine when to start and when to stop the sleep and wake processes for color shifting of pixels on the user's television screen.

In some embodiments, the video content to be modified by color shifting red and blue color values of the video content may be done at the central office (e.g., head end), whereby, based on the time of day when the video content is to be displayed, a manifest is obtained by a download server for a plurality of fragments containing video content tailored for the particular time of day when the video content is to be displayed. For example, if a movie is to be shown at noon, then a first manifest is obtained by the download server that includes a list of fragments to be obtained from a content server. Each fragment comprises a file containing video and/or audio of a small portion (e.g., two seconds) of a video program, whereby the fragments are played in a consecutive manner to display an entire program (e.g., a two hour movie comprising 3600 fragments). The fragments may be sent by the download server to a user's television for display, in which video content in those fragments are not color shifted. If the same movie is to be shown at 11:00 p.m., which is past the user's typical bed time, then a second manifest is obtained by the download server, whereby the second manifest includes a different list of fragments to be obtained from the content server. The video content of the fragments in the second manifest are such that the red color amount of pixels comprising the video content is increased and the blue color amount of pixels comprising the video content is decreased as compared to corresponding pixels comprising the video content of the fragments in the first manifest for the movie shown at noon. If the same movie is to be shown at 7 a.m., which is around the user's typical wake time, then a third manifest is obtained by the download server that includes a third list of fragments to be obtained from the content server, in which video content of the fragments in the third manifest are such that the red color amount of pixels comprising the video content is decreased and the blue color amount of pixels comprising the video content is increased as compared to corresponding pixels comprising the video content of the fragments in the first manifest for the movie shown at noon. In these embodiments, the color shifting of pixels is performed at the source (e.g., app server 107 or data server 106 as shown in FIG. 1), and not at the premises of the user watching the video content. This provides for less complexity at the user's set top box, and also may be useful for providing the same color-shifted video content for a particular geographical region that experiences the same sunset time and the same sunrise time.

In some embodiments, the video content to be modified by color shifting red and blue colors may be done at the set top box (STB), by applying a particular filter to the video content received from the head end (e.g., video content received from the download server) to color shift pixels to be output by the television based on the time of day when the video content is to be displayed.

In some embodiments, the video content to be modified based on the time of day when the video content is to displayed may be done at the television itself, such as by applying a user setting that adjusts the red and blue color content of the television display. This may be done by way of a ' color settings' user input via the user's remote control device that is received by HDMI Cable Pin 13, which corresponds to a Consumer Electronics Control Channel that may be used by the user to adjust the color of video content to be displayed by the television.

In some embodiments, the light intensity and/or the brightness of the video content to be displayed on the user's television or computer display may be shifted based on when the video content is displayed as compared to when the user is predicted to go to sleep. For example, the light intensity of the video content may be linearly decreased by 1% per minute starting 30 minutes prior to sunset, whereby the light intensity of the video content may be decreased to a particular amount, such as 50% below the unadjusted light intensity at 31 minutes prior to sunset, and remains at that level until the user turns off the television and goes to bed. This may be performed together with the red and blue shifting of pixels colors, to increase the likelihood that the user will become sleepy and go to bed.

In a similar manner, the sound level of the television or computer may be decreased starting at a particular time prior to when the user is predicted to go to sleep, to encourage the user to go to bed. For example, the sound level of the television may be linearly decreased by 1% per minute starting 30 minutes prior to when the user is predicted to go to sleep, whereby the sound level may be decreased to a particular amount, such as 50% below the unadjusted sound level at 31 minutes prior to when the user is predicted to go to sleep (the predicted sleep time), and remains at that level until the user turns off the television and goes to bed. This may be performed together with the red and blue color shifting of pixels and/or the light intensity modification of the video content, to further increase the likelihood that the user will become sleepy and go to bed.

In some embodiments, based on the location the television in a user's house and information as to who occupies a room in which the television is located, such as the room for a 12 year old child, the video content may be color shifted based on typical sleep times for a 12 year old child, or based on another user, such as a parent, providing parental control information that may be used to modify the video content. For example, in a first room occupied by a 12 year old child, the video content may be color shifted to increase the red content of pixels and decrease the blue content of pixels starting at 8 p.m., whereas in a second room occupied by a 16 year old child, the video content may be color shifted to increase the red content of pixels and decrease the blue content of pixels starting at 9 p.m. This bed time information may be provided by a parent to a home security system or other smart home system, using a particular code known only to the parent for inputting such information. In a similar manner, wake time information may be input by the parent for each child so as to increase the blue content of pixels and decrease the red content of pixels starting at a particular time in the morning, to make the child more awake prior to leaving the house to go to school.

In some embodiments, the lighting in the room where the user is watching television may also be modified such that the red and blue spectrums of the light may be color-shifted in the same manner as the video content provided to the television of the user, to enhance the 'sleep aid' features when the user is watching television with color-shifted video content just prior to or after the time when the user is predicted to go to sleep, or to enhance 'wake aid' features when the user is watching television with color-shifted video content during daylight hours.

Figure 9:
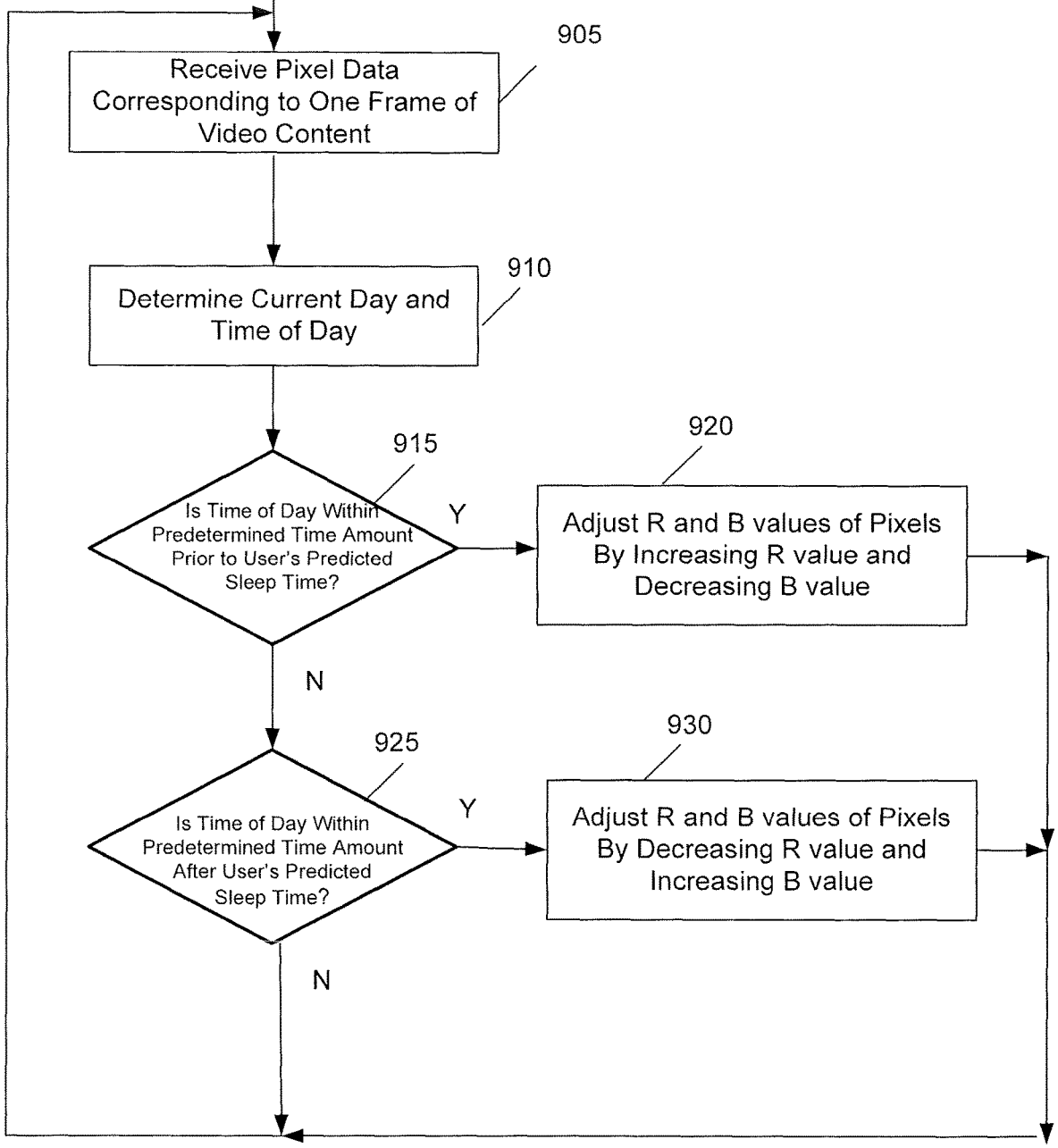
FIG. 9 is a flow diagram describing how pixel color shifting may be used to enhance wakefulness or sleepiness based on the time of day when a user is viewing content, according to one or more illustrative aspects of the disclosure.

FIG. 9 is a flow diagram of a method of modifying video content based on closeness in time of day to a user's predicted sleep time, according to an embodiment. In step 905, pixel data corresponding to one frame of video content is received. For example, the one frame of video content may be received for display on a computer display or television. In step 910, the current time of day is determined. In step 915, a determination is made as to whether the current time of day is within a predetermined time amount prior to the user's predicted sleep time (e.g., 30 minutes prior to sunset, or 30 minutes prior to a time when the user's home security system transitions to a high alert state from a normal alert state). If the determination in step 915 is Yes, then in step 920 a color shift is applied to pixels to be displayed in a frame of video content on the computer display or television by adjusting R and B values of pixels to be displayed by increased the R value and decreasing the B value, and the process returns to step 905 to await receipt of the next frame of video content. If the determination in step 915 is No, then the process proceeds to step 925. In step 925, a determination is made as to whether the current time of day is within a predetermined time amount after the user's predicted sleep time (e.g., 30 minutes after sunrise, or 30 minutes after when the user's home security system transitions to a high alert state from a normal alert state). If the determination in step 925 is Yes, then in step 930 a color shift is applied to pixels to be displayed in a frame of video content on the computer display or television by adjusting R and B values of pixels to be displayed by decreasing the R value and increasing the B value, and the process returns to step 905 to await receipt of the next frame of video content. If the determination in step 925 is No, then the process returns to step 905 to await receipt of the next frame of video content.

In some embodiments, only a portion of the video content may be color shifted, so as to provide video that includes color shifted pixels that enhance the sleep aid aspects while watching video content during night hours or that enhance wake aid aspects while watching video content in the morning or during daylight hours, but which also provide for a portion of the video content that is unmodified and thus easy on the user's eyes. In some embodiments, the color shifting of pixels may be gradually done for different parts of the screen. For example, the color shifting of pixels may be applied to just a small part in the middle of the screen, and then gradually the color shifting of pixels may expand outwardly on the screen so that eventually the pixels comprising the entire screen are color shifted. Alternatively, the color shifting of pixels may be applied to just a small peripheral portion on the outer edges of the screen, and then gradually the color shifting of pixels may expand inwardly on the screen so that eventually the pixels comprising the entire screen are color shifted.

Figure 10:
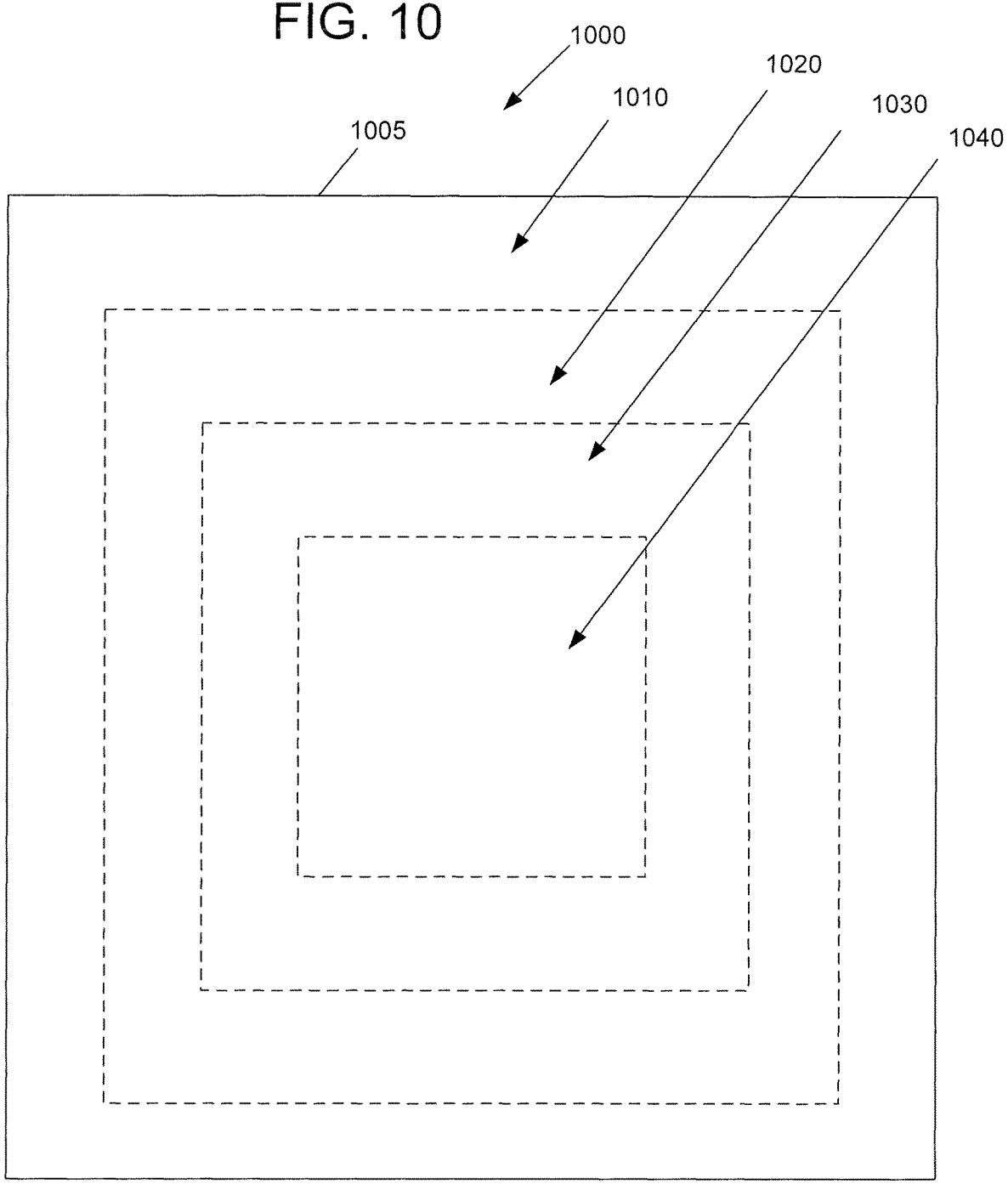
FIG. 10 shows display sections in which pixels within different portions of a display are color-shifted over time to enhance wakefulness or sleepiness based on the time of day when a user is viewing content, according to one or more illustrative aspects of the disclosure.

The example above shifted color values of a screen based on time. In some examples, the color shifting can also occur gradually at different parts of the screen. For example, as sleep time approaches, the pixels at the periphery of a screen may shift before the pixels at the center of the screen. This gradual easing may also help adjust the user for sleep. Referring now to FIG. 10, at a predetermined time prior to the time when the user is predicted to go to sleep, such as 30 minutes prior to the time when the user is predicted to go to sleep, the pixels within a portion of the video content to be displayed as a frame of video on the user's television are color shifted. That color shifted portion may comprise pixels located at an outer peripheral portion 1010 of a frame 1000 of video content for display on the user's television set, such as an outer 10% rectangular region of the frame of video. The outer peripheral portion 1010 of the frame 1000 of video content is adjacent to an outer edge 1005 of the frame 1000 of video content.

As the time of day approaches the time when the user is predicted to go to sleep, the portion of the video content to be color shifted may be increased. The increase in the portion of the video content to be color shifted may be accomplished, for example, by increasing the outer rectangular region by 1% for each minute after the predetermined time prior to the predicted sleep time. Thus, for example, at 15 minutes prior to the time when the user is predicted to go to sleep, the outer portion of the frame of video content having pixels to be color shifted is of a size equal to 10%+(15*1)%=25%, and thus pixels within an outer 25% rectangular region of the frame of video are color shifted at 15 minutes prior to the time when the user is predicted to go to sleep. The region in which pixels are color shifted may correspond to the combination of outer rectangular regions 1010 and 1020 in FIG. 10.

The portion of the video content to be color shifted may be increased by starting with an outer, peripheral portion of the video content, and then moving inward to thereby increase a size of the color-shifted video content as time progresses. For example, at the time when the user is predicted to go to sleep, the outer portion of the frame 1000 of video content having pixels to be color shifted is of a size equal to 10%+(30*1)%=40%, and thus pixels within an outer 40% rectangular region of the frame of video are color shifted at 15 minutes prior to the time when the user is predicted to go to sleep. The region in which pixels are color shifted may correspond to the combination of outer rectangular regions 1010, 1020 and 1030 in FIG. 10, whereby the rectangular region 1040 in the center of the frame 1000 of video would be the only region of the frame 1000 that contains pixels that are not color shifted.

After the time when the user is predicted to go to sleep, the frame of video content to be displayed may be increased at the same rate as done prior to the time when the user is predicted to go to sleep, until the entire frame of video content is color shifted. In some embodiments, the color shifting of pixels may be performed at the same rate as described with respect to other embodiments, whereby the number of pixels to be color shifted is increased to cover a greater amount of the frame of video content displayed. In other embodiments, the color shifting of pixels may be maintained at the same amount starting at the predetermined time prior to the time when the user is predicted to go to sleep, whereby the only change in how the video content is to be displayed is the amount of the frame of video content that is to be displayed with the color shifted pixels based on the time when the frame of video content is to be displayed as compared to the time when the user is predicted to go to sleep.

Figure 11:
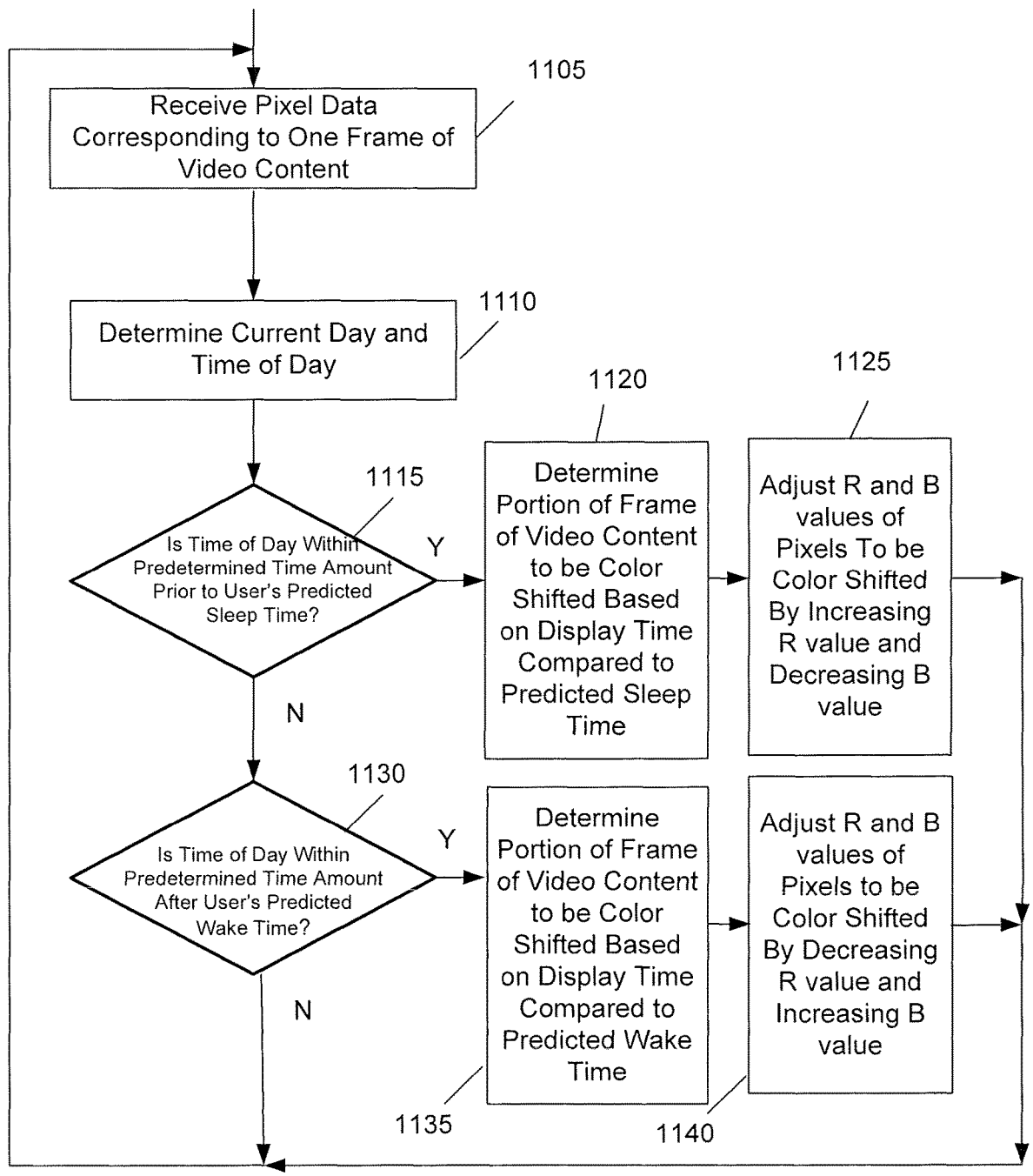
FIG. 11 is a flow diagram showing the process for color-shifting different portions of a display over time to enhance wakefulness or sleepiness based on the time of day when a user is viewing content, according to one or more illustrative aspects of the disclosure.

In some example, a portion of a frame of video content to be color shifted is determined based on the time when the video content is to be displayed, in which the both the amount of the video content and the pixels making up the video content to be color shifted are gradually changed to make the viewing of the color-adjusted video content reasonably acceptable to the viewer. FIG. 11 is a flow diagram of a method of modifying a portion of a frame of video content based on closeness in time of day to the user is predicted to go to sleep or to awake from sleep, according to an embodiment. In step 1105, pixel data corresponding to one frame of video content is received. For example, the pixel data may be received for display on a computer display or television. In step 1110, the current time of day is determined. In step 1115, a determination is made as to whether the current time of day is within a predetermined time amount prior to the time when the user is predicted to go to sleep (e.g., 30 minutes prior to the time when the user is predicted to go to sleep). If the determination in step 1115 is Yes, then in step 1120 a portion of the frame of video content to be color shifted is determined, and in step 1125 a color shift is applied to pixels to be displayed in the portion of the frame of video content on the computer display or television by adjusting R and B values of pixels to be displayed in that portion by increased the R value and decreasing the B value. After step 1125 is completed, the process returns to step 1105 to await receipt of the next frame of video content. If the determination in step 1115 is No, then the process proceeds to step 1130. In step 1130, a determination is made as to whether the current time of day is within a predetermined time amount after the time when the user is predicted to go to awake from sleep (e.g., 30 minutes after the time when the user is predicted to go to awake from sleep). If the determination in step 1130 is Yes, then in step 1135 a portion of the frame of video content to be color shifted is determined, and in step 1140 a color shift is applied to pixels to be displayed in the portion of the frame of video content on the computer display or television by adjusting R and B values of pixels be displayed in that portion by decreasing the R value and increasing the B value. After step 1140 is completed, the process returns to step 1105 to await receipt of the next frame of video content. If the determination in step 1130 is No, then no color shifting of received frame of video content is performed, and the process returns to step 1105 to await receipt of the next frame of video content.

In some embodiments, the modification of advertisement video and/or audio may be performed in a different manner than non-advertisement video and/or audio displayed just prior to and just after the advertisement is displayed. For example, if the video content is modified such that pixels are color shifted to increase the red color content due to the video content being displayed at or after the user's typical bed time, the advertisement portions of the video content may not be adjusted, or may be color-shifted to increase the blue color content such that the user is made more awake when watching the advertisement portions as compared to watching other non-advertisement portions of the video content on the user's television. The level of blue-shifting may be provided in a manner such that the more the advertiser pays a content provider for a particular advertisement to be displayed, the stronger the increase of the blue color-shifting that is made for the advertisement portions of the video content. This may result in more revenue being provided for the content provider, based on advertisers paying more for their advertisements that are color shifted to make those advertisements stand out more as compared to the non-advertisement portions of the video content provided prior to and after the advertisement portions of the video content. In some embodiments, the advertiser may pay the content provider a fee to not modify their advertisement at all, whereas the non-advertisement content provided to the user before and after the advertisement may be color shifted in a manner as described with respect to one or more embodiments described in this application.

In some embodiments, based on the genre of the video content, such as whether the video content corresponds to an action movie or whether the video content corresponds to a romantic movie, color shifting of pixels comprising the video content may or may not be performed. The genre of the video content may be obtained from □guide□information associated with the video content, which may include information as to whether the video content includes violence, mature subject matter, nudity, etc. For example, if a user is watching an action movie past his or her normal bedtime, the user probably does not want to be sleepy while he/she is watching the action movie, and thus color shifting of pixels may not be performed for □action movie□genres. On the contrary, if the user is watching a romantic movie well past his or her normal bedtime, the user probably does not mind to become sleepy while he/she is watching the romantic movie, and thus color shifting of pixels may be performed in this instance in a manner as described above with respect to different embodiments. Further, if the user is watching a sports program, then the amount of color shifting to be made on the video content provided to the user may be in a lesser or a greater amount as compared to different type of genre such as a comedy program that the user may watch at the same point in time during the day.

In some embodiments, each user device accessing a gateway that provides video content via a network (e.g., a WAN or LAN) may have their own sleep cycle settings, in which the gateway determines which device or devices the video content is intended for. Based on the sleep cycle settings for the device(s) to receive the video content, a gateway, such as gateway 111 in FIG. 1, may adjust the color content of pixels making up the video content in accordance with a user's sleep cycle settings associated with each device that receives the video content. In some embodiments, the gateway may output the same video content (e.g., a particular pay-per-view movie) to different users, in which each user receives color-shifted video content specifically tailored the sleep cycle settings of that user. Accordingly, a first user that receives video content output by the gateway for display by the first user's television, for the same pay-per-view movie at the same time of day as a second user that receives video content output by the gateway for display by the second user's television, may receive different color-shifted pixels for one or more frames of the video content. This difference is due to differences in sleep times (and thus the amount, if any, of pixel color shifting to be applied by the gateway) of the first and second users, with such user sleep time information being accessible by the gateway. By way of example, the gateway may determine which device IDs are to receive specific video content, such as a pay-per-view movie at a particular day and time-of-day, and, based on the characteristics of each the device associated with each device ID (e.g., an R,G,B display for Device ID #1, an R,G,B,Y display for Device ID #2), and based on a user is sleep and wake cycle information associated with each device ID, the gateway outputs video content to each device that is tailored to the specific device and to a user's sleep and/or wake cycle information that is associated with each specific device. FIG. 16 shows an embodiment in which a device ID may be used (see step 1610) to associate video content to be displayed by multiple devices associated with multiple users, in which each user has a sleep process or wake process created based on predicted sleep time or predicted wake time for that user.

Figure 12:
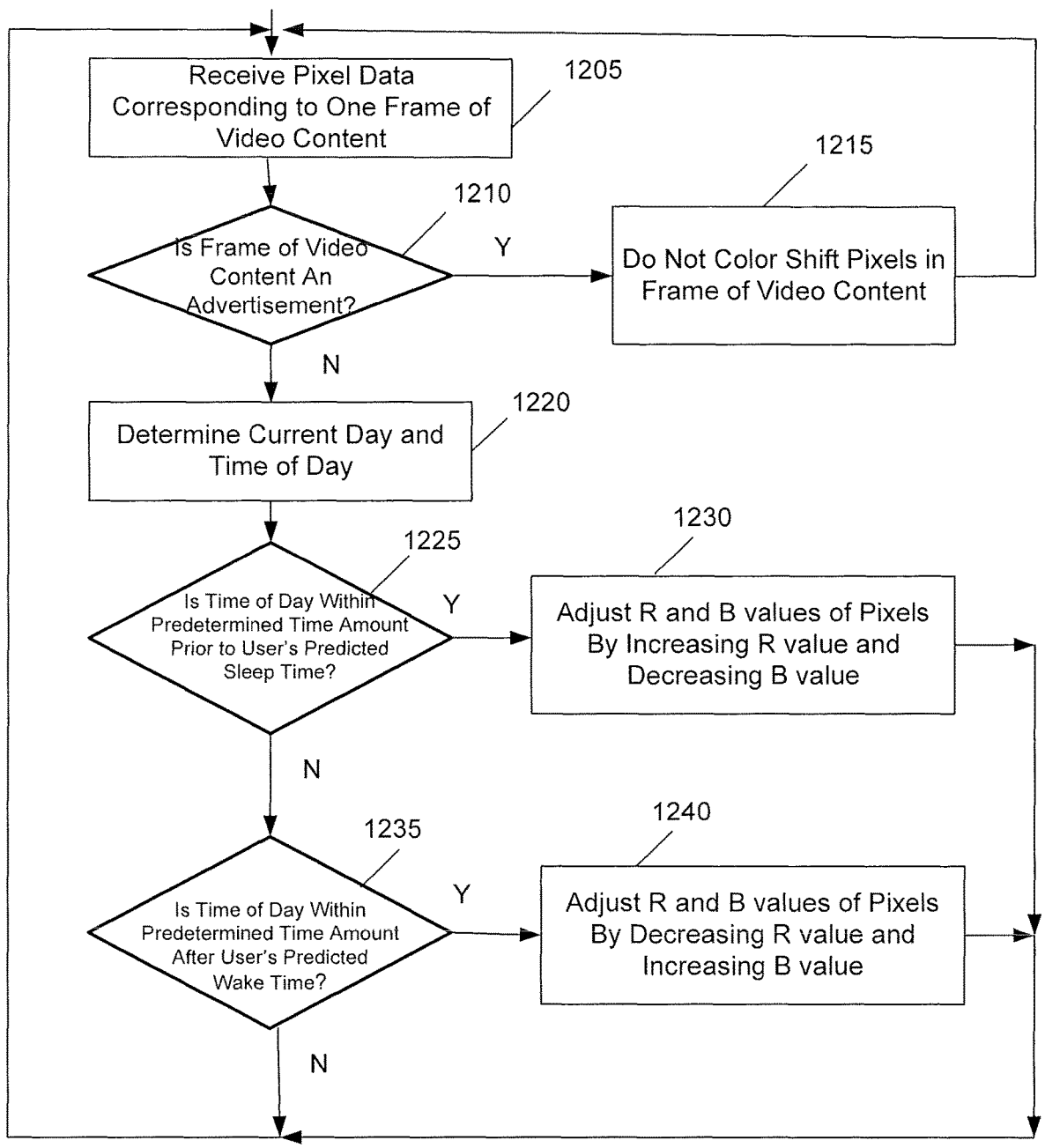
FIG. 12 is a flow diagram in which advertisement content is not color-shifted while other portions of video content are color-shifted to enhance a user's wakefulness or sleepiness, according to one or more illustrative aspects of the disclosure.

FIG. 12 is a flow diagram of a method of modifying video content based on closeness in time to a user's predicted wake time and the user's predicted sleep time, and based on the type of video content to be displayed, according to an embodiment. In step 1205, pixel data corresponding to one frame of video content is received. For example, the pixel data may be received for display on a computer display or television. In step 1210, a determination is made as to whether the frame of video content received corresponds to an advertisement. The determination of which frames of video content comprise an advertisement and which frames of video content do not comprise an advertisement may be accomplished by any of a variety of methods for distinguishing one type of video content over another type of video content received by a STB or a television or computer, such as by information in a particular data field of a frame of the video content signifying whether the frame comprises advertisement data or non-advertisement data (e.g., a frame of data of a movie watched by a user). If the determination in step 1210 is Yes, then the flow proceeds to step 1215, in which (after verifying that the advertiser has paid or has agreed to pay the content provider for not modifying the advertiser's advertisement) the pixels comprising the pixels within a frame of video content to be displayed are not color shifted, and whereby the process proceeds to step 1205 to await the next frame of video content. If the determination in step 1210 is No, such as if the video content comprises one frame of a movie, the flow proceeds to step 1220, in which the current time of day is determined. In step 1225, a determination is made as to whether the current time of day is within a predetermined time amount prior to the time when the user is predicted to go to sleep (e.g., 30 minutes prior to the time when the user is predicted to go to sleep). If the determination in step 1225 is Yes, then in step 1230 a color shift is applied to pixels to be displayed in a frame of video content on the computer display or television by adjusting R and B values of pixels to be displayed by increased the R value and decreasing the B value, and then the process returns to step 1205 to await the next frame of video content. If the determination in step 1225 is No, then the process proceeds to step 1235. In step 1235, a determination is made as to whether the current time of day is within a predetermined time amount after the time when the user is predicted to go to wake from a sleep state (e.g., 30 minutes after the time when the user is predicted to awake from a sleep state). If the determination in step 1235 is Yes, then in step 1240 a color shift is applied to pixels to be displayed in a frame of video content on the computer display or television by adjusting R and B values of pixels to be displayed by decreasing the R value and increasing the B value, and then the process returns to step 1205 to await the next frame of video content. If the determination in step 1235 is No, then no color shifting of pixels within a received frame of video content is performed, and the process returns back to step 1205 to await receipt of the next frame of video content.

In a similar manner, web site owners may have their web site content color shifted according to one or more embodiments described herein, to enhance a user's sleep state who has recently viewed or is currently viewing a web page at night. This can be done, for example, by gradually increasing the red color content of the web page in an amount based on a viewing time as compared to the user's predicted sleep time. Also, web site owners may have their web site content color shifted to enhance a user's wake state who has recently viewed or is currently viewing a web page during the day. This can be done, for example, after the user has awaken from a sleep state and is viewing the web page, by gradually increasing the blue color content of the web page in an amount based on a viewing time as compared to the user's predicted wake time.

Further, movie content providers may have their video content color shifted according to one or more embodiments described herein, to enhance a user's sleep state or a user's wake state based on the time when the user is viewing the content, as compared to the user's predicted sleep time and the user's predicted wake time.

Figure 13:
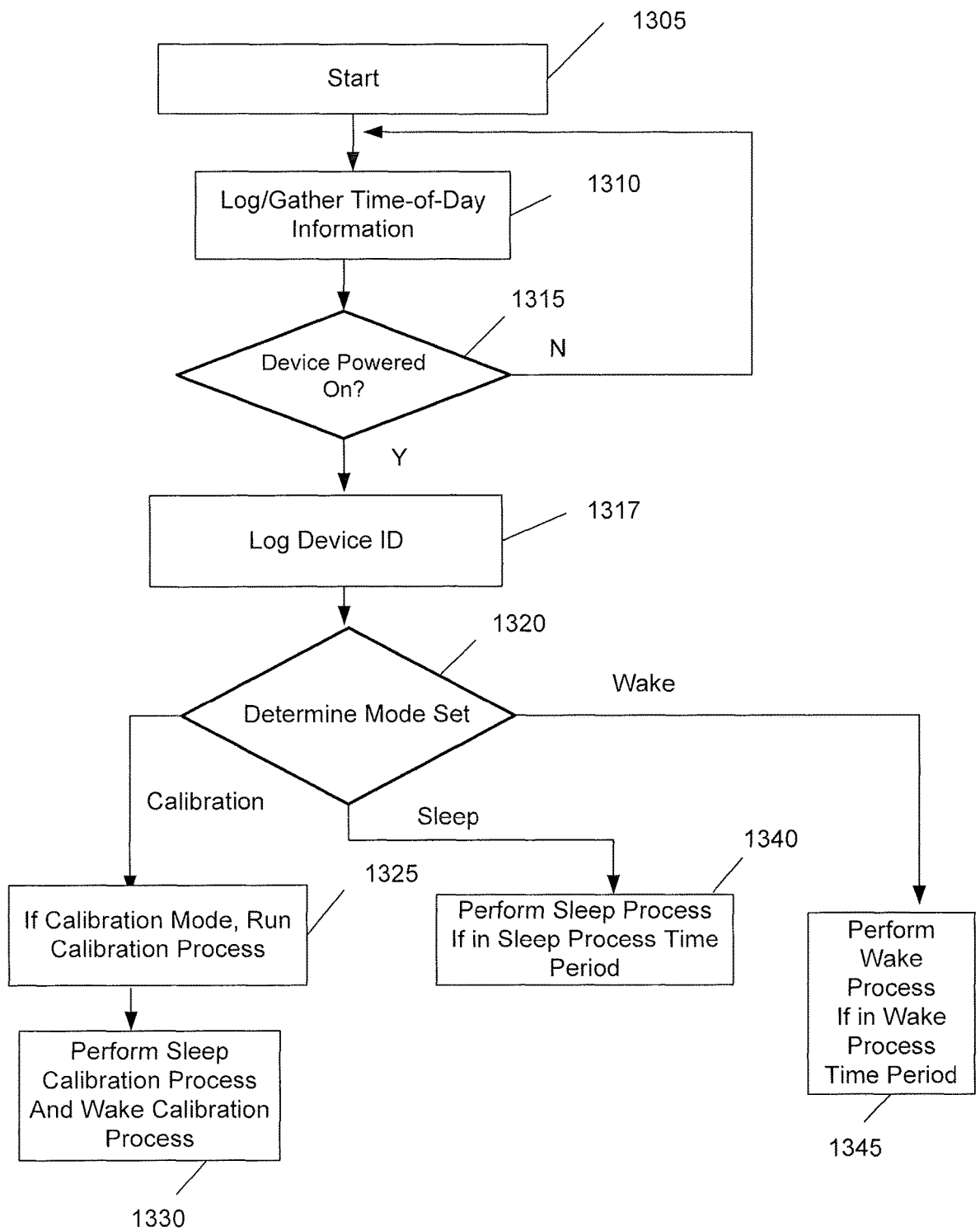
FIG. 13 is a flow diagram of a method of providing color-shifting of video content to enhance a user's wakefulness or sleepiness, according to one or more illustrative aspects of the disclosure.

A calibration process may be used determine an appropriate amount of color-shifting of video content. FIG. 13 is a flow diagram of a method of providing color-shifting of video content to enhance a user's sleep state or a user's wake state that uses a calibration process. In step 1305, the method starts. In step 1310, time-of-day (TOD) information is logged and gathered. The TOD information may be logged into a user profile, and gathered from previous user data, geolocation data, and/or home security data. TOD information may be obtained from multiple devices associated with multiple users, in which a sleep mode and a wake mode may be tailored for each of the users based on the TOD information obtained for each user. In step 1315, the device ID is determined (e.g., is device an HD television, a Plasma television, is device a RGB display, is device a RBGW display, is device a RGBY display, is device a lighting device, etc.). Based on the determination, the device ID is logged (stored) in step 1317, which may be used to collect usage data for that device to determine optimum wake and sleep time periods associated with a user of that device, as well as to determine the particular type of wake process or sleep process to perform. In step 1320, the current mode for the device is determined. The current mode may be an auto-calibration mode, a user-defined sleep mode, or a user-defined wake mode. For the user-defined sleep mode and the user-defined wake mode, associated user-defined times for the user's typical sleep time and wake time are obtained (e.g., based on the logged usage information for that device over the past two weeks). If the current mode is the auto-calibration mode, then a run calibration process is performed in step 1325, whereby a sleep process in which pixels are color shifted to obtain sleep calibration data and a wake process in which pixels are color shifted to obtain wake calibration data are run in step 1330. If the current mode is either a sleep mode or a wake mode, then, based on the current time as compared to a user-defined typical sleep time and a user-defined typical wake time, a sleep process is performed in step 1340 or a wake process is performed in step 1345, in which pixels are color shifted to enhance a user's sleepiness or wakefulness. The calibration mode may be used to optimize the color shifting of pixels to be performed on video content to be provided to a user, based on most recently obtained TOD information associated with the user.

Figure 14:
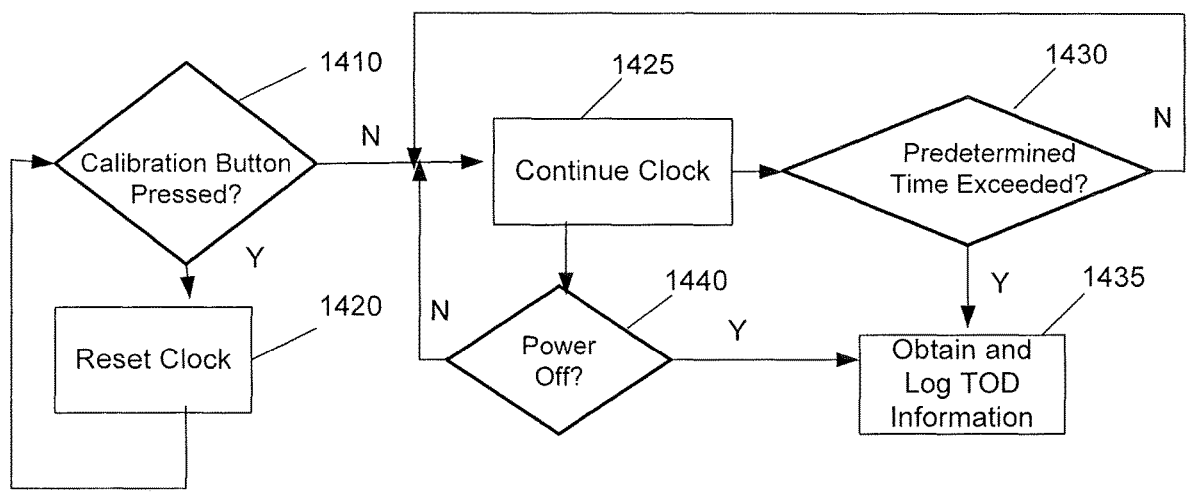
FIG. 14 is a flow diagram showing a sleep or wake calibration process performed according to one or more illustrative aspects of the disclosure.

A calibration process may be performed periodically, such as every two months, in order to optimize the process for color shifting of pixels based on most recent usage data of a user who will be viewing the color shifted video content. FIG. 14 is a flow diagram showing details of the run calibration process performed in step 1325 of FIG. 13. In step 1410, a determination is made as to whether a calibration button is pressed (e.g., pressed by a user instructed to invoke a calibration process every two months), such as a calibration button provided on a set top box associated with a television being viewed by a user, or a calibration option selected by the user via a remote control device. If Yes, then a clock is reset in step 1420, and the process returns to step 1410 to start a new calibration time period. If No, then the clock continues to run in step 1425 for an existing calibration process in which TOD data is obtained and logged during the entire calibration time period, as provided in step 1435. Powering off of the device (e.g., turning off a television set and/or set top box) in step 1440, or the predetermined calibration time period ending in step 1430, results in logging of the calibration data obtained during the calibration time period. The TOD information obtained and logged in step 1435 of FIG. 14 during the calibration mode may be utilized in step 1310 of FIG. 13.

Figure 15:
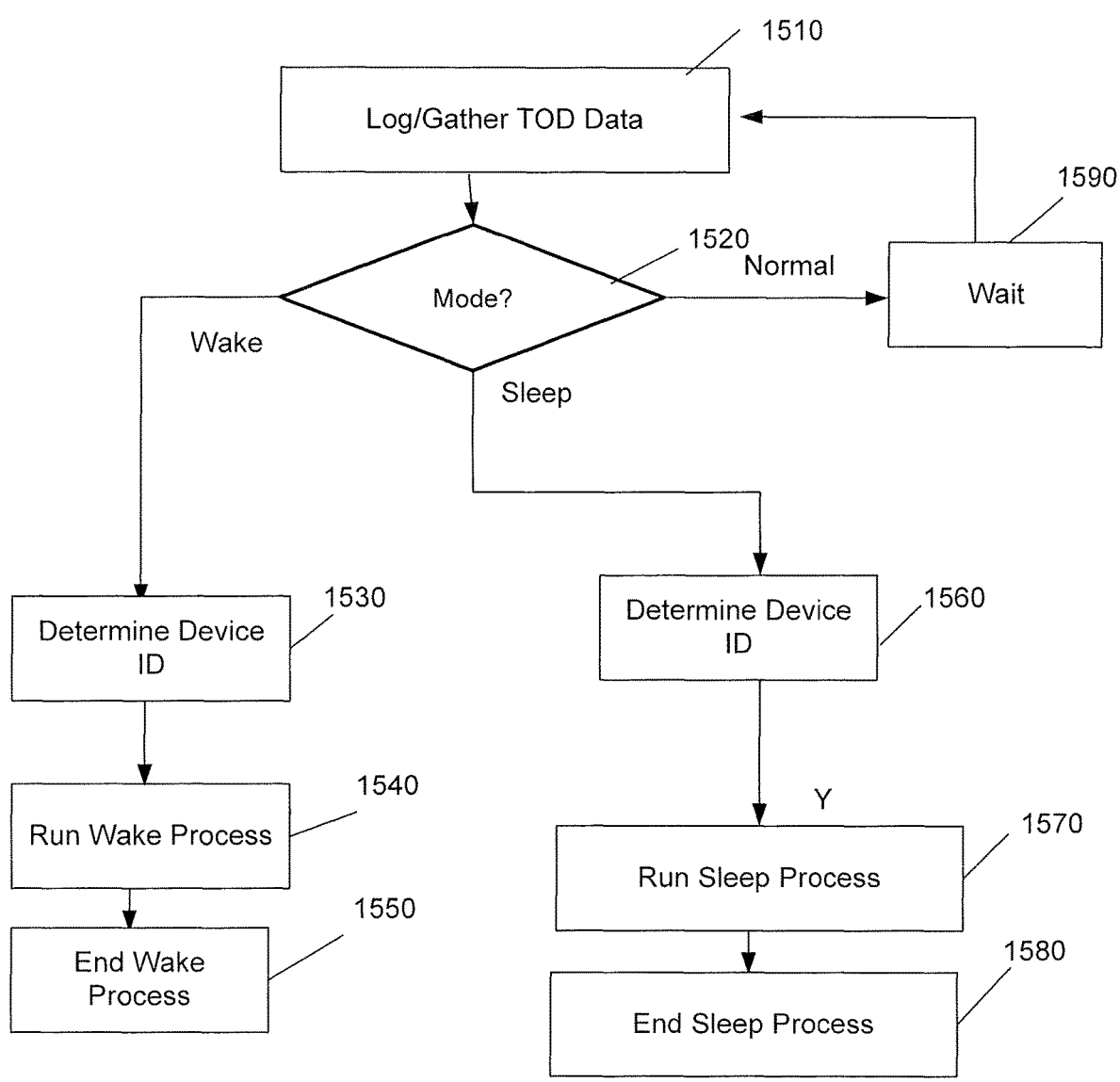
FIG. 15 is a flow diagram of the steps that may be performed to provide for color-shifted video content, according to one or more illustrative aspects of the disclosure.

One aspect of performing color shifting of pixels is determining when a user is predicted to sleep and when the user is predicted to awake from sleep, whereby usage data of devices associated with the user may be used to make such predictions. FIG. 15 is a flow diagram of the steps that may be performed to provide for color-shifted video content, according to an embodiment. In step 1510, time-of-day (TOD) data with respect to usage of a device (e.g., device is ON from 8 a.m. to 10 a.m., and is OFF from 10 a.m. to noon, etc.) is logged and gathered. In step 1520, the current mode is determined based on the current time of day as compared to the TOD data. If the current mode is a wake mode, based on the current time of day and the TOD data, and based on the device type (e.g., a television having an RGB display, or a television having a RGBY display, or a lamp that only outputs visible light and does not output video content, etc.) as determined in step 1530, a wake process is run in step 1540, and the wake process ends in step 1550 when the user turns off the device or the wake process time period has ended. If the current mode is a sleep mode, based on the current time of day and the TOD data, and based on the device type as determined in step 1560, a sleep process is run in step 1570, and the sleep process ends in step 1580 when the user turns the device OFF or the sleep process time period has ended. If the current mode is a normal mode, in which color shifting of pixels is not to be performed, such as a time during the middle of the day far from the user's normal wake time and the user's normal sleep time, then no color shifting of pixels is performed, but whereby the process enters a wait state in step 1590 and returns to step 1510 to continue to collect TOD data of the user. The TOD data may be used predict a user's normal sleep time and/or the user's normal wake time.

FIG. 16 is a flow diagram showing different types of pixel color shifting that may be performed according to an embodiment, based on the type of device for which video content is to be displayed to a user. Multiple devices each having its own device ID may have video content color shifted to assist in a user's sleep or wake state, whereby each device ID may be associated with a particular user having a preferred sleep time and a preferred wake time. In step 1610, a device type is determined (e.g., a LCD, LED, Plasma, or HD television having an RGB display, or a LCD, LED, Plasma, or HD television having a RGBY display, or a LCD, LED 4K UHD, or Plasma television having an RGBW display, or a lamp that outputs visible light and does not output video content, etc.), and based on logged information associated with the device (e.g., historical data obtained over the previous two weeks regarding ON and OFF times of the device during the day), either an RGB pixel color-shifting process is performed, an RBGW pixel color-shifting process is performed, an RGBY pixel color-shifting process is performed, a light intensity shifting process is performed (which may be performed together with the pixel color-shifting process), or no pixel color-shifting or light intensity shifting process is performed.

If the RGB pixel color-shifting process is to be performed as determined from the device ID, then logged usage information associated with the device (e.g., historical data obtained over the previous two weeks regarding ON and OFF times of the device during the day) is obtained in step 1620, and a sleep process or a wake sleep process is performed in step 1665 based on the logged usage information.

If the RGBW pixel color-shifting process is to be performed as determined from the device ID, then logged usage information associated with the device (e.g., historical data obtained over the previous two weeks regarding ON and OFF times of the device during the day) is obtained in step 1630, and a sleep process or a wake sleep process is performed in step 1870 based on the logged usage information.

If the RGBY pixel color-shifting process is to be performed as determined from the device ID, then logged usage information associated with the device (e.g., historical data obtained over the previous two weeks regarding ON and OFF times of the device during the day) is obtained in step 1640, and a sleep process or a wake sleep process is performed in step 1675 based on the logged usage information.

If the light intensity shifting process is to be performed as determined from the device ID (e.g., the device is a lamp), then logged information associated with the device (e.g., historical data obtained over the previous two weeks regarding ON and OFF times of the lamp during the day) is obtained in step 1650, and a sleep light process or a wake light sleep process is performed in step 1680 based on the logged information. If no pixel color-shifting or light intensity-shifting process is to performed, then the process ends in step 1860, whereby video content and light intensity are provided to the user unadjusted.

Provided below are equations that may be used to color shift pixels for different types of displays, according to one or more embodiments. An RGB pixel color-shifting that may be performed in some embodiments may be applied to such displays as LCD, LED, Plasma, and HD screens/devices/front panels, for example. An RGB pixel color-shifting sleep process that is performed in step 1665 of FIG. 16 when it is determined that the current time-of-day is around a user's typical sleep time may be performed using equations 1, 2, 3 below.

$$R_F = R_I + P_R\left(\frac{255 - R_I}{255}\right) \quad (1)$$

$$G_F = G_I + P_G\left(I_{G_I}\left(\frac{X_{B-R} + 1}{2}\right) + D_{G_I}\left(\frac{X_{B-R} - 1}{2}\right)\right) \quad (2)$$

$$B_F = B_I - P_B\left(\frac{B_I}{255}\right) \quad (3)$$

where $$X_{B-R} = \frac{B_F - R_F - .1}{\sqrt{(B_F - R_F - .1)^2}}$$

$$I_{G_I} = \left(\frac{255 - G_I}{255}\right)$$

$$D_{G_I} = \left(\frac{G_I}{255}\right)$$

$$P_R = P_{R_{Int}}\left(\frac{T_{C_{sec}}}{T_{S_{sec}}}\right)$$

$$P_G = P_{G_{Int}}\left(\frac{T_{C_{sec}}}{T_{S_{sec}}}\right)$$

$$P_B = P_{B_{Int}}\left(\frac{T_{C_{sec}}}{T_{S_{sec}}}\right)$$

where
- $R_F$=Red (R) value (0 to 255) post modification
- $R_I$=Red (R) value (0 to 255) pre-modification
- $B_F$=Blue (B) value (0 to 255) post modification
- $B_I$=Blue (B) value (0 to 255) pre-modification
- $G_F$=Green (G) value (0 to 255) post modification
- $G_I$=Green (G) value (0 to 255) pre-modification
- $X_{B-R}$=B vs R comparison (Which is bigger?)Result: −1 or 1
- $I_{G_I}$=Increase G value % calculation,
- $D_{G_I}$=Decrease G value % calculation
- P=Linear RGB color shift intensity, based on time till sleep,
- $P_{int}$=RGB color shift intensity constant,
- $T_{C_{Sec}}$=The Current Time in Seconds (0 to 86400)
- $T_{S_{sec}}$=The upcoming (or recently passed) Time in Seconds of "Sleep Time"

From the equations above, R is increased, with a max of 255, while B is decreased with a min value of 0, while G is either increased or decreased based on if B or R is larger, such that when B is greater than R, an increase in G is beneficial to the final color, while when R is greater than B, a decrease in G is beneficial. By way of the above pixel color-shift equations, increase in G slides the pixel color toward the middle of the wavelength spectrum, thereby providing a desirable color-shifted video image while at the same time increasing sleepiness in a sleep mode or wakefulness in a wake mode. In the above equations, the −0.1 value in the G calculation prevents all potential 'divide by 0' scenarios, with a slight bias towards decreasing the G value. Also, the R,G,B pixel color values calculated by way of the above equations, and in the equations provided below for other embodiments, may be rounded to the nearest integer value before being injected as a color-shifted pixel onto a television display or computer display (e.g., the R pixel value of 155.3 is rounded down to 155, and the G pixel value of 73.8 is rounded up to 74).

An RGB pixel color-shifting wake process according to some embodiments that may be performed in step 1665 of FIG. 16 when it is determined that the current time-of-day is around a user's typical wake time may be performed using equations 4, 5 and 6 below.

$$R_F = R_I - P_R\left(\frac{R_I}{255}\right) \quad (4)$$

$$G_F = G_I + P_G\left(I_{G_I}\left(\frac{X_{R-B} + 1}{2}\right) + D_{G_I}\left(\frac{X_{R-B} - 1}{2}\right)\right) \quad (5)$$

$$B_F = B_I + P_B\left(\frac{255 - B_I}{255}\right) \quad (6)$$

where $$X_{R-B} = \frac{R_F - B_F - .1}{\sqrt{(R_F - B_F - .1)^2}}$$

$$I_{G_I} = \left(\frac{255 - G_I}{255}\right)$$

$$D_{G_I} = \left(\frac{G_I}{255}\right)$$

$$P_R = P_{R_{Int}}\left(\frac{T_{W_{sec}}}{T_{C_{sec}}}\right)$$

$$P_G = P_{G_{Int}}\left(\frac{T_{W_{sec}}}{T_{C_{sec}}}\right)$$

$$P_B = P_{B_{Int}}\left(\frac{T_{W_{sec}}}{T_{C_{sec}}}\right)$$

where
- $R_F$=Red (R) value (0 to 255) post modification
- $R_I$=Red (R) value (0 to 255) pre-modification
- $B_F$=Blue (B) value (0 to 255) post modification
- $B_I$=Blue (B) value (0 to 255) pre-modification
- $G_F$=Green (G) value (0 to 255) post modification
- $G_I$=Green (G) value (0 to 255) pre-modification
- $X_{R-B}$=R vs B comparison (Which is bigger?)Result: −1 or 1
- $I_{G_I}$=Increase G value % calculation
- $D_{G_I}$=Decrease G value % calculation
- P=Linear RGB color shift intensity, based on time till sleep
- $P_{int}$=RGB color shift intensity constant
- $T_{C_{Sec}}$=The Current Time in Seconds (0 to 86400)
- $T_{S_{sec}}$=The normal "wake up" time in Seconds (0 to 86400)

A light intensity shifting process according to some embodiments that is performed in step 1650 of FIG. 16 may be performed using the following equations 7, 8 in an embodiment, and may be applied all types of devices. According to this embodiment, the light is shifted to extra bright when the time is close to wake time, and is shifted to dim when the time is close to sleep time of a user, whereby the light intensity is changed slowly to result in a smooth transitioning of the light intensity to aid in a wake assist or sleep assist pixel color-shifting process that may be performed at the same time.

$$BN_{F_I} = BN_I + P_{BN_W}\left(\frac{100 - BN_I}{100}\right) \quad (7)$$

$$BN_{F_D} = BN_I - P_{BN_S}\left(\frac{BN_I}{100}\right) \quad (8)$$

(Brightness BN may vary from 0 to 100),
where $$P_{BN_W} = P_{BN_I}\left(\frac{T_{W_{sec}}}{T_{C_{sec}}}\right)$$

-continued $$P_{BN_S} = P_{BN_I}\left(\frac{T_{C_{sec}}}{T_{S_{sec}}}\right)$$

$BN_{F_I}$=Final Brightness after Increase (0 to 100)
$BN_{F_D}$=Final Brightness after Decrease (0 to 100)
$P_{BN_{Wake/Sleep}}$=Linear Brightness shift intensity, based on time till/from event
$P_{BN_I}$=Brightness intensity constant An RGBW pixel color-shifting that may be performed in some embodiments may be applied to such displays LCD, LED 4K UHD, and Plasma Screens, for example. An RGBW pixel color-shifting sleep process that may be performed in step 1630 of FIG. 16 when it is determined that the current time-of-day is around a user's typical sleep time may be performed using the equations 9–12 below.

$$R_F = R_I + P_R\left(\frac{255 - R_I}{255}\right) \quad (9)$$

$$G_F = G_I + P_G\left(I_{G_I}\left(\frac{X_{B-R}+1}{2}\right) + D_{G_I}\left(\frac{X_{B-R}-1}{2}\right)\right) \quad (10)$$

$$B_F = B_I - P_B\left(\frac{B_I}{255}\right) \quad (11)$$

$$W_F = W_I - P_W\left(\frac{W_I}{255}\right) \quad (12)$$

where $$X_{B-R} = \frac{B_F - R_F - .1}{\sqrt{(B_F - R_F - .1)^2}}$$

$$I_{G_I} = \left(\frac{255 - G_I}{255}\right)$$

$$D_{G_I} = \left(\frac{G_I}{255}\right)$$

$$P_R = P_{R_{Int}}\left(\frac{T_{C_{sec}}}{T_{S_{sec}}}\right)$$

$$P_G = P_{G_{Int}}\left(\frac{T_{C_{sec}}}{T_{S_{sec}}}\right)$$

$$P_B = P_{B_{Int}}\left(\frac{T_{C_{sec}}}{T_{S_{sec}}}\right)$$

$$P_W = P_{W_{Int}}\left(\frac{T_{C_{sec}}}{T_{S_{sec}}}\right)$$

where
$R_F$=Red (R) value (0 to 255) post modification
$R_I$=Red (R) value (0 to 255) pre-modification
$B_F$=Blue (B) value (0 to 255) post modification
$B_I$=Blue (B) value (0 to 255) pre-modification
$G_F$=Green (G) value (0 to 255) post modification
$G_I$=Green (G) value (0 to 255) pre-modification
$W_F$=White (W) value (0 to 255) post modification
$W_I$=White (W) value (0 to 255) pre-modification
$X_{B-R}$=B vs R comparison (Which is bigger?)Result: −1 or 1
$I_{G_I}$=Increase G value % calculation
$D_{G_I}$=Decrease G value % calculation
P=Linear RGBW color shift intensity, based on time till sleep
$P_{int}$=RGB color shift intensity constant
$T_{C_{Sec}}$=The Current Time in Seconds (0 to 86400)
$T_{S_{sec}}$=The upcoming (or recently passed) Time in Seconds of "Sleep Time"

For the RGBW pixel color-shifting as provided above, similar to the impact of Brightness on sleep cycles, a decrease in the White sub-pixel intensity may improve sleepiness of the content viewer.

An RGBW pixel color-shifting wake process that may be performed according to some embodiments in step 1630 of FIG. 16 may be applied to such displays LCD, LED 4K UHD, and Plasma Screens according to an embodiment when it is determined that the current time-of-day is around a user's typical wake time, and may be performed using the equations 13-16 below.

$$R_F = R_I - P_R\left(\frac{R_I}{255}\right) \quad (13)$$

$$G_F = G_I + P_G\left(I_{G_I}\left(\frac{X_{R-B}+1}{2}\right) + D_{G_I}\left(\frac{X_{R-B}-1}{2}\right)\right) \quad (14)$$

$$B_F = B_I + P_B\left(\frac{255 - B_I}{255}\right) \quad (15)$$

$$W_F = W_I + P_W\left(\frac{255 - W_I}{255}\right) \quad (16)$$

where $$X_{R-B} = \frac{R_F - B_F - .1}{\sqrt{(R_F - B_F - .1)^2}}$$

$$I_{G_I} = \left(\frac{255 - G_I}{255}\right)$$

$$D_{G_I} = \left(\frac{G_I}{255}\right)$$

$$P_R = P_{R_{Int}}\left(\frac{T_{W_{sec}}}{T_{C_{sec}}}\right)$$

$$P_G = P_{G_{Int}}\left(\frac{T_{W_{sec}}}{T_{C_{sec}}}\right)$$

$$P_B = P_{B_{Int}}\left(\frac{T_{W_{sec}}}{T_{C_{sec}}}\right)$$

$$P_W = P_{W_{Int}}\left(\frac{T_{W_{sec}}}{T_{C_{sec}}}\right)$$

where
$R_F$=Red (R) value (0 to 255) post modification
$R_I$=Red (R) value (0 to 255) pre-modification
$B_F$=Blue (B) value (0 to 255) post modification
$B_I$=Blue (B) value (0 to 255) pre-modification
$G_F$=Green (G) value (0 to 255) post modification
$G_I$=Green (G) value (0 to 255) pre-modification
$W_F$=White (W) value (0 to 255) post modification
$W_I$=White (W) value (0 to 255) pre-modification
$X_{R-B}$=B vs R comparison (Which is bigger?)Result: −1 or 1
$I_{G_I}$=Increase G value % calculation
$D_{G_I}$=Decrease G value % calculation
P=Linear RGBW color shift intensity, based on time till sleep
$P_{int}$=RGBW color shift intensity constant
$T_{C_{Sec}}$=The Current Time in Seconds (0 to 86400)
$T_{S_{sec}}$=The upcoming (or recently passed) Time in Seconds of "Sleep Time"

For the RGBW pixel color-shifting as provided above, similar to the impact of Brightness on sleep cycles, an increase in the White sub-pixel intensity may improve wakefulness of the content viewer.

An RGBY pixel color-shifting that may be performed may be applied to such displays LCD, LED, HD, and Plasma Screens, for example. An RGBY pixel color-shifting sleep process that may be performed according to some embodiments in step 1640 of FIG. 16 when it is determined that the current time-of-day is around a user's typical sleep time may be performed using the equations 17-20 below.

$$R_F = R_I + P_R\left(\frac{255 - R_I}{255}\right) \tag{17}$$

$$G_F = G_I + P_G\left(I_{G_I}\left(\frac{X_G + 1}{2}\right) + D_{G_I}\left(\frac{X_G - 1}{2}\right)\right) \tag{18}$$

$$B_F = B_I - P_B\left(\frac{B_I}{255}\right) \tag{19}$$

$$Y_F = Y_I + P_Y\left(I_{Y_I}\left(\frac{X_Y + 1}{2}\right) + D_{Y_I}\left(\frac{X_Y - 1}{2}\right)\right) \tag{20}$$

where $$X_G = \frac{B_F - R_F - \frac{Y_I}{2} - .1}{\sqrt{\left(B_F - R_F - \frac{Y_I}{2} - .1\right)^2}}$$

$$I_{G_I} = \left(\frac{255 - G_I}{255}\right)$$

$$D_{G_I} = \left(\frac{G_I}{255}\right)$$

$$X_Y = \frac{3 * B_F + G_I - R_F - .1}{\sqrt{(3 * B_F + G_I - R_F - .1)^2}}$$

$$I_{Y_I} = \left(\frac{255 - Y_I}{255}\right)$$

$$D_{Y_I} = \left(\frac{Y_I}{255}\right)$$

$$P_R = P_{R_{Int}}\left(\frac{T_{C_{sec}}}{T_{S_{sec}}}\right)$$

$$P_G = P_{G_{Int}}\left(\frac{T_{C_{sec}}}{T_{S_{sec}}}\right)$$

$$P_B = P_{B_{Int}}\left(\frac{T_{C_{sec}}}{T_{S_{sec}}}\right)$$

$$P_Y = P_{Y_{Int}}\left(\frac{T_{C_{sec}}}{T_{S_{sec}}}\right)$$

where
$R_F$=Red (R) value (0 to 255) post modification
$R_I$=Red (R) value (0 to 255) pre-modification
$B_F$=Blue (B) value (0 to 255) post modification
$B_I$=Blue (B) value (0 to 255) pre-modification
$G_F$=Green (G) value (0 to 255) post modification
$G_I$=Green (G) value (0 to 255) pre-modification
$Y_F$=Yellow (Y) value (0 to 255) post modification
$Y_I$=Yellow (Y) value (0 to 255) pre-modification
$X_G$=Weighted comparison of sub-pixels to adjust green impact (Result: −1 or 1)
$I_{G_I}$=Increase G value % calculation
$D_{G_I}$=Decrease G value % calculation
$X_Y$=Weighted comparison of sub-pixels to adjust yellow impact (Result: −1 or 1)
$I_{Y_I}$=Increase Y value % calculation
$D_{Y_I}$=Decrease Y value % calculation
P=Linear RGBY color shift intensity, based on time till sleep
$P_{int}$=RGBY color shift intensity constant
$T_{C_{Sec}}$=The Current Time in Seconds (0 to 86400)
$T_{S_{sec}}$=The upcoming (or recently passed) Time in Seconds of "Sleep Time"

From the equations above, R is increased, with a max of 255, while B is decreased with a min value of 0, while G and Y are either increased or decreased based on ideal impact analysis with respect to displaying color-shifted video content to a user while at the same time assisting the user's sleepiness.

An RGBY pixel color-shifting wake process that may be performed may be applied to such displays LCD, LED, HD, and Plasma Screens, for example. The RGBY pixel color-shifting wake process that may be performed in step 1640 in FIG. 16 may be performed according to an embodiment when it is determined that the current time-of-day is around a user's typical sleep time may be performed using the equations 21-24 below $$R_F = R_I - P_R\left(\frac{R_I}{255}\right) \tag{21}$$

$$G_F = G_I + P_G\left(I_{G_I}\left(\frac{X_G + 1}{2}\right) + D_{G_I}\left(\frac{X_G - 1}{2}\right)\right) \tag{22}$$

$$B_F = B_I + P_B\left(\frac{255 - B_I}{255}\right) \tag{23}$$

$$Y_F = Y_I + P_Y\left(I_{Y_I}\left(\frac{X_Y + 1}{2}\right) + D_{Y_I}\left(\frac{X_Y - 1}{2}\right)\right) \tag{24}$$

where $$X_G = \frac{R_F + \frac{Y_I}{2} - B_F - .1}{\sqrt{\left(R_F + \frac{Y_I}{2} - B_F - .1\right)^2}}$$

$$I_{G_I} = \left(\frac{255 - G_I}{255}\right)$$

$$D_{G_I} = \left(\frac{G_I}{255}\right)$$

$$X_Y = \frac{R_F - 3 * B_F - G_I - .1}{\sqrt{(R_F - 3 * B_F - G_I - .1)^2}}$$

$$I_{Y_I} = \left(\frac{255 - Y_I}{255}\right)$$

$$D_{Y_I} = \left(\frac{Y_I}{255}\right)$$

$$P_R = P_{R_{Int}}\left(\frac{T_{W_{sec}}}{T_{C_{sec}}}\right)$$

$$P_G = P_{G_{Int}}\left(\frac{T_{W_{sec}}}{T_{C_{sec}}}\right)$$

$$P_B = P_{B_{Int}}\left(\frac{T_{W_{sec}}}{T_{C_{sec}}}\right)$$

$$P_Y = P_{Y_{Int}}\left(\frac{T_{W_{sec}}}{T_{C_{sec}}}\right)$$

where
$R_F$=Red (R) value (0 to 255) post modification
$R_I$=Red (R) value (0 to 255) pre-modification
$B_F$=Blue (B) value (0 to 255) post modification
$B_I$=Blue (B) value (0 to 255) pre-modification
$G_F$=Green (G) value (0 to 255) post modification
$G_I$=Green (G) value (0 to 255) pre-modification
$Y_F$=Yellow (Y) value (0 to 255) post modification $Y_f$=Yellow (Y) value (0 to 255) pre-modification
$X_G$=Weighted comparison of sub-pixels to adjust green impact (Result: −1 or 1)
$I_{G_I}$=Increase G value % calculation
$D_{G_I}$=Decrease G value % calculation
$X_Y$=Weighted comparison of sub-pixels to adjust yellow impact (Result: −1 or 1)
$I_{Y_I}$=Increase Y value % calculation
$D_{Y_I}$=Decrease Y value % calculation
P=Linear RGBY color shift intensity, based on time till sleep
$P_{int}$=RGBY color shift intensity constant
$T_{C_{Sec}}$=The Current Time in Seconds (0 to 86400)
$T_{S_{sec}}$=The upcoming (or recently passed) Time in Seconds of "Sleep Time"

From the equations above, B is increased, with a max of 255, while R is decreased with a min value of 0, while G and Y are either increased or decreased based on if B or R is larger, which provides for beneficial color shifts of R, G, B and Y to aid in a user's wakefulness when watching video content comprising pixels color-shifted in this manner.

FIG. 17 is a chart showing the changes in pixel color values R, G, and B, from a starting pixel R,G,B color value of 102, 102, 204, to an ending pixel color R,G,B color value of 255, 0, 0, for a first example case where a user is watching video content around the user's normal sleep time, and whereby the pixel color values are shifted to red to enhance the user's sleepiness. The initial color value of 102, 102, 204 corresponds to a purpleish-blue color, whereby the pixel color value shifts to a lavender color, then to a gray color, then to a light red color, then to a red color, and then to a deep red color.

Figure 18:
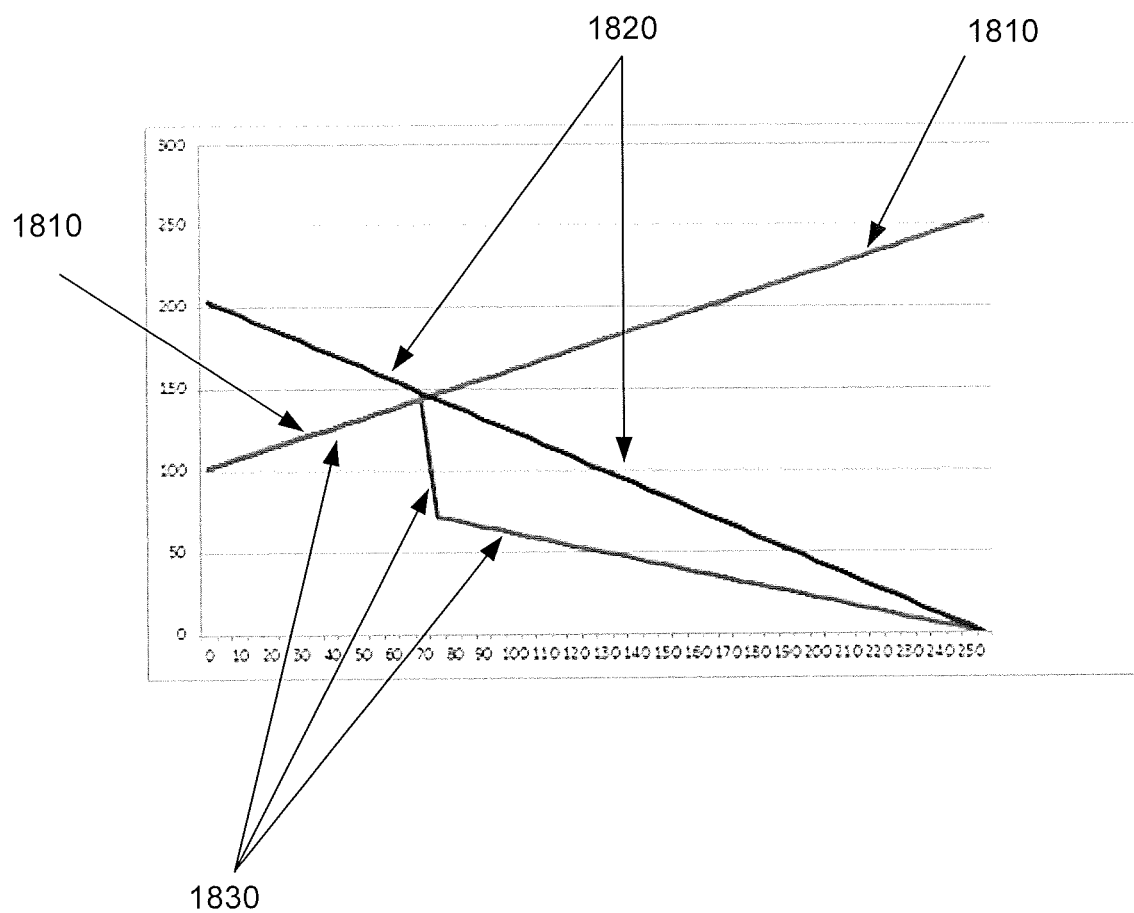
FIG. 18 is a plot of the red, green and blue color values of the pixel of the first example as shown in FIG. 17, showing how those values change linearly over time, according to one or more illustrative aspects of the disclosure.
Figure 20:
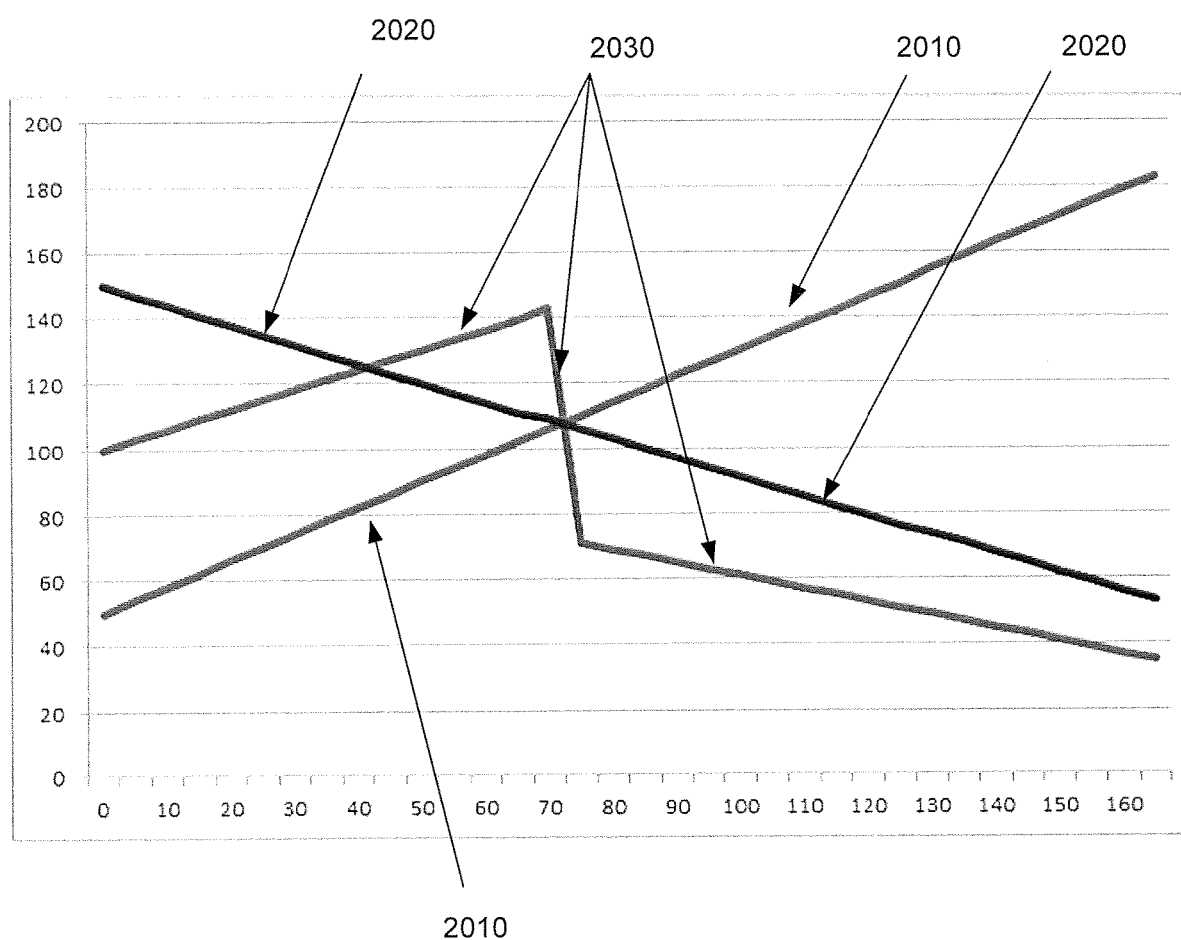
FIG. 20 is a plot of the red, green and blue color values of the pixel of the second example as shown in FIG. 19, showing how those values change linearly over time, according to one or more illustrative aspects of the disclosure.

FIG. 18 is a plot showing the change in pixel color value based on the data provided in FIG. 17, whereby the red color value of a pixel is linearly increased over time as shown by plot 1810, the blue color value of the pixel is linearly decreased over time as shown by plot 1820, and the green color value of the pixel is initially increased, then decreased at a large rate, and then decreased at a slower rate as shown by plot 1830. This results in a display of a video image over time that does not vary too much over time but that gradually provides for a greater red color of the video content to aid in a user's sleepiness while viewing the video content. As shown in FIG. 18, the red pixel value increases linearly from 102 to 204 over the sleep process interval. The green pixel value increases from 100 to 144 over a first portion of the sleep process interval, then sharply decreases linearly to a value of 72 over a short second portion of the sleep process interval, and then decreases linearly to a value of 0 over a third portion of the sleep process interval. The change in the 'green' pixel color value over the sleep process interval as shown in FIG. 20 is due to the inventor's finding that adding more green (which pulls the overall color of the pixel towards a center wavelength in the visible color spectrum) goes from being a benefit to a detriment with respect to sleep enhancement. The point at which the green color of the pixel goes from steadily increasing to steadily decreasing is the point at which the red color of the pixel has increased to a value that is greater than the blue color of the pixel (that has been decreasing from the time when the television was turned ON up to the user's typical sleep time).

FIG. 19 is a chart showing the changes in pixel color values R, G, and B, from a starting pixel R,G,B color value of 50, 100, 150, to an ending pixel color R,G,B color value of 183, 35, 53, for a second example case where a user is watching video content around the user's normal sleep time, and whereby the pixel color values are shifted to red to enhance the user's sleepiness. The initial color value of 50, 100, 150 corresponds to a greenish-blue color, whereby the pixel color value shifts to a dark green color, then to a light green color, then to a light red color, and then to a red color, and then to a deep red color.

FIG. 20 is a plot showing the change in pixel color value based on the data provided in FIG. 19, whereby the red color value of a pixel is linearly increased over time as shown by plot 2010, the blue color value of the pixel is linearly decreased over time as shown by plot 2020, and the green color value of the pixel is initially increased, then decreased at a large rate, and then decreased at a slower rate (similar to the rate at which the blue color value is decreased) as shown by plot 2030. This results in a display of a video image over time that does not vary too much over time but that gradually provides for a greater red color of the video content to aid in a user's sleepiness while viewing the video content. As shown in FIG. 20, the red pixel value increases linearly from 50 to 183 over the sleep process interval. The green pixel value increases from 100 to 143 over a first portion of the sleep process interval, then sharply decreases linearly to a value of 71 over a short second portion of the sleep process interval, and then decreases linearly to a value of 35 over a third portion of the sleep process interval. Similar to the plot as shown in FIG. 18, the change in the 'green' pixel color value as shown in FIG. 20 is due to the inventor's finding that adding more green (which pulls the overall color of the pixel towards a center wavelength in the visible color spectrum) goes from being a benefit to a detriment with respect to sleep enhancement. Similar to the discussion above with respect to FIG. 18, the point at which the green color of the pixel goes from steadily increasing to steadily decreasing is the point at which the red color of the pixel has increased to a value that is greater than the blue color of the pixel (that has been decreasing from the time when the television was turned ON up to the user's typical sleep time). For a wake process, the situation is the opposite from what is described above with respect to the change in the green pixel value over time for the sleep process.

FIG. 21 is a chart showing the time period at which the sleep pixel color-shift process is performed on video content, and the time periods at which the wake process pixel color-shift is performed on video content, according to an embodiment. In this example, the user's typical wake time is 7 a.m., and the user's typical sleep time is 10 p.m. At those two times, the intensity time factor applied to adjusting pixel color and light intensity is one (1). At time periods not close to the user's typical wake time and the user's typical sleep time, such as between 1 a.m. to 5 a.m. and between 11:30 a.m. and 7 p.m., video content is provided to the user's computer display or television without any pixel color shifting or light intensity being performed, since those times are when the user does not need wake enhancement or sleep enhancement. Starting at 7 p.m., which is 2 hours prior to the user's typical sleep time of 9 p.m., the intensity factor applied to pixel color shifting and light intensity gradually increases from the value 0.866 to 1 at 10 p.m., and further increases to a value of 1.136 at 1 a.m. is the user is still watching video at that time. This provides for a gradual increase in the redness of the video content up to a time when the user eventually goes to sleep, while at the same time maintaining a fairly watchable video content that is not changing to a mostly red color too fast. Similarly, starting at 5 a.m., which is 2 hours prior to the user's typical wake time of 7 a.m., the intensity factor applied to pixel color shifting and light intensity gradually decreases from the value 1.4 to 1 at 7 a.m., and further decreases to a value of 0.636 at 11 a.m., which is 2 hours past the typical time when the user turns off his/her home computer or television in the morning. This provides for a high intensity of blueness in video content when the user turns on a television in the early morning, which gradually decreases in intensity until the user eventually turns off the television later in the morning, to increase wakefulness while at the same time maintaining a fairly watchable video content that is not changing to a mostly blue color too fast.

With respect to the embodiments disclosed herein, the blue light spectrum may be defined within a wavelength range of from 450 to 495 nm, the green light spectrum may be defined within a wavelength range of from 495 to 570 nm, and the red light spectrum may be defined within a wavelength range of from 620 to 750 nm. The visible light spectrum may be defined within a wavelength range of from 350 nm (beginning of the violet light spectrum) to 750 nm (end of the red light spectrum).

The various features described above are merely non-limiting examples, and can be rearranged, combined, subdivided, omitted, and/or altered in any desired manner. For example, features of the computing device (including the remote control device and the terminal device) described herein can be subdivided among multiple processors and computing devices. Further, the display that includes video content to be color shifted may be a smart phone display, tablet computer display, or other type of display device that may display video content to a user, and that may utilize a video content color pixel display scheme other than the ones (e.g., a display screen other than an R,G,B display screen, an R,G,B,Y display screen, or an R,G,B,W display screen) utilized in the various embodiments described above. Also, the pixel adjusting may be modified based on a user's work times, whereby a user who works the night shift may have pixel color shifting to increase wakefulness during nighttime hours when the user is working (e.g., between the hours of 10 p.m. to 6 a.m.), and to increase sleepiness during daylight hours (e.g., between the hours of 7 a.m. to 6 p.m.) when the user is back at home and trying to get some rest. The true scope of this patent should only be defined by the claims that follow.

We claim:

1. A method comprising:
    receiving an indication that a computing device outputs video content, wherein the video content comprises information for a plurality of pixels each having a first color value and a second color value;
    determining a time in which the computing device outputs the video content;
    determining, based on historical viewing data associated with the computing device, a future time associated with a change associated with the computing device's output of video content; and
    sending, based on an amount of time between the time and the future time, an indication to change at least one of the first or the second color values of one or more of the plurality of pixels associated with the video content output by the computing device.

2. The method of claim 1, wherein the video content is to be sent using a Red, Green, Blue (R, G, B) format, and wherein the first and second color values respectively comprise Red and Blue color values, Red and Green color values, or Green and Blue color values.

3. The method of claim 1, wherein the method further comprises:
    adjusting, based on the amount of time between the time and the future time, at least one of an intensity or a brightness of the video content.

4. The method of claim 1, wherein the method further comprises:
    sending color values of larger portions of the video content as the time approaches the future time.

5. The method of claim 1, wherein the method further comprises determining the historical viewing data based on information indicating when a display screen changed from an ON state to an OFF state.

6. The method of claim 1, wherein sending the at least one of the first or the second color values comprises:
    increasing, in a linear manner as the amount of time decreases, a red color value of each of the plurality of pixels of the video content; and
    decreasing, in a linear manner as the amount of time decreases, a blue color value of each of the plurality of pixels of the video content.

7. The method of claim 1, wherein the video content is to be sent using a Red, Green, Blue, Yellow (R, G, B, Y) format, and wherein the first and second color values respectively comprise Red and Blue color values, Red and Yellow color values, Red and Green color values, Blue and Green color values, Blue and Yellow color values, or Green and Yellow color values.

8. The method of claim 1, wherein the video content is to be sent using a Red, Green, Blue, White (R, G, B, W) format, and wherein the first and second color values respectively comprise Red and Blue color values, Red and White color values, Red and Green color values, Blue and Green color values, Blue and White color values, or Green and White color values.

9. A method comprising:
    determining, by a computing device, a current time in which an output for video content is active outputting video content that comprises information for a plurality of pixels each having a first color value and a second color value;
    determining, based on historical viewing data associated with the computing device, a future time in which the output for video content is idle; and
    sending, based on an amount of time between the current time and the future time, at least one of the first or the second color values of at least one of the plurality of pixels of a portion of the video content.

10. The method of claim 9, wherein during the sending of the at least one of the first or the second color values, a first color value and a second color value for at least one other of the plurality of pixels are left unmodified.

11. The method of claim 9, wherein the video content is to be sent using a Red, Green, Blue, Yellow (R, G, B, Y) format, and wherein the first and second color values respectively comprise Red and Blue color values, Red and Yellow color values, Red and Green color values, Blue and Green color values, Blue and Yellow color values, or Green and Yellow color values.

12. The method of claim 9, wherein the method further comprises:
    adjusting at least one of an intensity or a brightness of the video content.

13. The method of claim 9, wherein sending the at least one of the first or the second color values is performed by a controller of a set top box associated with a television set that is to display the video content.

14. The method of claim 9, wherein the video content is to be sent using a Red, Green, Blue, White (R, G, B, W)

format, and wherein the first and second color values respectively comprise Red and Blue color values, Red and White color values, Red and Green color values, Blue and Green color values, Blue and White color values, or Green and White color values.

15. A method comprising:
receiving an indication that a computing device is outputting video content, wherein the video content comprises information for a plurality of pixels each having a color value;
determining a current time in which the computing device is outputting the video content;
determining, based on historical viewing data associated with the computing device, a future time in which a video content output of the computing device is idle; and
determining, based on an amount of time between:
the determined future time, and
the determined current time,
an amount of a color shift to apply to at least one of the plurality of pixels of the video content.

16. The method of claim 15, further comprising:
identifying a genre for which no color shift is to be applied.

17. The method of claim 15, wherein the video content is to be sent using a Red, Green, Blue, Yellow (R, G, B, Y) format, and wherein the determining the amount of the color shift to apply comprises:

determining to apply a color shift in a linear manner to a corresponding color value of one or more of the plurality of pixels of the video content, wherein the corresponding color value comprises at least one of Red, Green, Blue, or Yellow color values.

18. The method of claim 15, wherein the video content is to be sent using a Red, Green, Blue, White (R, G, B, W) format, and wherein the determining the amount of the color shift to apply comprises:

determining to apply a color shift in a linear manner to a corresponding color value of one or more of the plurality of pixels of the video content, wherein the corresponding color value comprises at least one of Red, Green, Blue, or White color values.

19. The method of claim 15, wherein the method further comprises:
adjusting, based on a difference in time between the determined future time and the determined current time, at least one of an intensity or a brightness of the video content.

20. The method of claim 15, wherein determining the amount of the color shift to apply to the at least one of the plurality of pixels of the video content is further based on a genre associated with the video content.

* * * * *

UNITED STATES PATENT AND TRADEMARK OFFICE
CERTIFICATE OF CORRECTION

PATENT NO.         : 10,589,057 B2
APPLICATION NO.    : 15/624806
DATED              : March 17, 2020
INVENTOR(S)        : Eng et al.

It is certified that error appears in the above-identified patent and that said Letters Patent is hereby corrected as shown below:

In the Specification

Column 2, Summary, Lines 61-62:
Delete "0☐255 R value, 0☐255G value, and 0☐ 255 B value" and insert --0 - 255 R value, 0- 255 G value, and 0 - 255 B value-- therefor Column 5, Detail Description, Line 5:
Delete "(DOC SIS)" and insert --(DOCSIS)-- therefor Column 7, Detailed Description, Line 21:
Delete "HBO☐ and ESPN☐" and insert --HBO™ and ESPN™-- therefor Column 8, Detailed Description, Lines 42-43:
Delete "0☐255 R value, 0☐255G value, and 0☐ 255 B value" and insert --0 - 255 R value, 0- 255 G value, and 0 - 255 B value-- therefor Column 9, Detailed Description, Line 5:
Delete "☐30 minutes before sleep☐" and insert --"30 minutes before sleep"-- therefor Column 9, Detailed Description, Line 36:
Delete "#5" and insert --#58-- therefor Column 9, Detailed Description, Line 60:
Delete "☐X+" and insert --"X+-- therefor Column 9, Detailed Description, Line 62:
Delete "time)" and insert --time)"-- therefor Column 10, Detailed Description, Line 4:
Delete ")☐(" and insert --)-(-- therefor Signed and Sealed this
Seventh Day of March, 2023

*Katherine Kelly Vidal*
Katherine Kelly Vidal
*Director of the United States Patent and Trademark Office*

CERTIFICATE OF CORRECTION (continued)
U.S. Pat. No. 10,589,057 B2

Column 10, Detailed Description, Line 15:
Delete "☐Y" and insert --"Y-- therefor Column 10, Detailed Description, Line 16:
Delete "time)☐" and insert --time)"-- therefor Column 10, Detailed Description, Lines 25-26:
Delete ")☐(" and insert --)-(-- therefor Column 11, Detailed Description, Line 40:
Delete "☐normal☐mode to a ☐high alert☐ mode" and insert --"normal" mode to a "high alert" mode-- therefor Column 11, Detailed Description, Line 46:
Delete "☐high alert☐ mode" and insert --"high alert" mode-- therefor Column 12, Detailed Description, Line 40:
Delete "☐355☐" and insert --"355"-- therefor Column 12, Detailed Description, Line 61:
Delete "television 2" and insert --television #2-- therefor Column 13, Detailed Description, Line 19:
Delete "☐Settings☐" and insert --"Settings"-- therefor Column 13, Detailed Description, Line 21:
Delete "☐Turn Pixel Color Shifting Feature ON☐" and insert --"Turn Pixel Color Shifting Feature ON"-- therefor Column 13, Detailed Description, Line 25:
Delete "☐Settings☐" and insert --"Settings"-- therefor Column 13, Detailed Description, Lines 25-26:
Delete "☐Turn Pixel Color Shifting Feature OFF☐" and insert --"Turn Pixel Color Shifting Feature OFF"-- therefor Column 14, Detailed Description, Line 29:
Delete "' color settings'" and insert --'color settings'-- therefor Column 15, Detailed Description, Line 22:
Delete "' sleep" and insert --'sleep-- therefor Column 18, Detailed Description, Line 29:
Delete "☐guide☐" and insert --"guide"-- therefor

CERTIFICATE OF CORRECTION (continued)
U.S. Pat. No. 10,589,057 B2

Column 18, Detailed Description, Line 36:
Delete "□action movie□" and insert --"action movie"-- therefor Column 19, Detailed Description, Line 9:
Delete "ID #1," and insert --ID#1,-- therefor Column 19, Detailed Description, Line 10:
Delete "ID #2)," and insert --ID#2),-- therefor Column 25, Detailed Description, Line 17:
Delete "9□12" and insert --9 - 12-- therefor Column 28, Detailed Description, Line 62:
Delete "$R_l$" and insert --$R_I$-- therefor